(12) United States Patent
Belleau et al.

(10) Patent No.: US 6,175,008 B1
(45) Date of Patent: Jan. 16, 2001

(54) PROCESSES FOR PREPARING SUBSTITUTED 1,3-OXATHIOLANES WITH ANTIVIRAL PROPERTIES

(75) Inventors: Bernard Belleau, deceased, late of Westmount, by Pierrette Belleau, executrix; Tarek Mansour, Montreal; Allan Tse, Ville St-Laurent; Colleen A. Evans, Montreal; Haolun Jin, Pierrefonds; Boulos Zacharie, Laval des Rapides; Nghe Nguyen-Ba, La Prairie, all of (CA)

(73) Assignee: BioChem Pharma Inc., Laval (CA)

( * ) Notice: Under 35 U.S.C. 154(b), the term of this patent shall be extended for 0 days.

(21) Appl. No.: 08/466,329

(22) Filed: Jun. 6, 1995

Related U.S. Application Data

(60) Division of application No. 08/040,163, filed on Mar. 29, 1993, now Pat. No. 5,466,806, which is a continuation-in-part of application No. 07/564,160, filed on Aug. 7, 1990, now abandoned, which is a continuation-in-part of application No. 07/546,676, filed on Jun. 29, 1990, now Pat. No. 5,041,449, and a continuation-in-part of application No. 07/308,101, filed on Feb. 8, 1989, now Pat. No. 5,047,407, which is a continuation of application No. 07/179,615, filed on Apr. 11, 1988, now abandoned.

(51) Int. Cl.[7] ............ C07D 327/04; C07D 411/04; C07D 473/06; C07D 473/18

(52) U.S. Cl. .......... 544/264; 544/265; 544/266; 544/267; 544/269; 544/270; 544/271; 544/272; 544/276; 544/277; 544/280; 544/310; 544/311; 544/312; 544/313; 544/314; 544/316; 544/317; 544/318; 544/327; 549/30

(58) Field of Search ............ 544/265, 266, 544/267, 269, 270, 280, 310, 317, 313; 549/30

(56) References Cited

U.S. PATENT DOCUMENTS

| | | | | |
|---|---|---|---|---|
| 3,328,388 | * | 6/1967 | Shen et al. | 760/211.5 |
| 4,415,573 | | 11/1983 | Ochi et al. | 544/310 |
| 5,204,466 | * | 4/1993 | Liotta et al. | 544/317 |
| 5,210,085 | | 5/1993 | Liotta et al. | 544/310 |
| 5,466,806 | * | 11/1995 | Belleau et al. | 544/310 |
| 5,684,164 | * | 11/1997 | Belleau | 549/30 |
| 5,763,606 | * | 6/1998 | Mansour | 544/264 |
| 5,914,400 | * | 6/1999 | Liotta et al. | 544/314 |

FOREIGN PATENT DOCUMENTS

| | | |
|---|---|---|
| 0 071 926 A1 | 7/1982 | (EP) . |
| 0 337 713 | 10/1989 | (EP) . |
| 0 382 526 | 2/1990 | (EP) . |
| 0 515 156 A1 | 5/1992 | (EP) . |
| 0 515 157 A1 | 5/1992 | (EP) . |
| WO 90/01492 | 2/1990 | (WO) . |
| WO 91/11186 | 8/1991 | (WO) . |
| WO 91/17159 | 11/1991 | (WO) . |
| WO 92/10496 | 6/1992 | (WO) . |
| WO 92/10497 | 6/1992 | (WO) . |
| WO 92/14729 | 9/1992 | (WO) . |
| WO 92/14743 | 9/1992 | (WO) . |
| WO 92/18517 | 10/1992 | (WO) . |
| WO 92/19246 | 11/1992 | (WO) . |
| WO 92/20669 | 11/1992 | (WO) . |
| WO 92/20696 | 11/1992 | (WO) . |
| 9414802 | * 7/1994 | (WO) . |

OTHER PUBLICATIONS

Fessenden, R. J. et al. *Organic Chemistry*, (Willard Grant Press, Boston), p. 633 (1983).*

Kraus, Jean Louis: Attardo, Giorgio, Synthesis (11), 1046–8 1991.*

J. Milton et al, Tet. Let., 1995,38, 6961.*

H. Jin et al, J. Org. Chem., 1995, 60, 2621–2623.*

J.W. Beach et al., "Synthesis of Enantiomerically Pure (2'R,5'S)–(–)–1–[2–(Hydroxymethyl)oxathiolan–5–yl]cytosine as a Potent Antiviral Agent Against Hepatitis B Virus (HBV) and Human Immunodeficiency Virus (HIV)", *J.Org. Chem.*, vol. 57, pp. 2217–2219 (1992).

B.R. Belleau, et al., "Oxidative Degradation of L–Ascorbic Acid Acetals to 2',3'–Dideoxy–3'–Oxaribofuranosides. Synthesis of Enantiomerically Pure 2',3'–Dideoxy–3'–Oxacytidine Stereoisomers as Potential Antiviral Agents", *Tetrahedron Lett.*, vol. 33, pp. 6949–6952 (1992).

A.D. Borthwick et al., "Synthesis and Enzymatic Resolution of Carbocyclic 2'–Ara–fluoro–Guanosine: A Potent New Anti–Herpetic Agent", *J.Chem.Soc.Chem.Commun.*, pp. 656–658 (1988).

C.K. Chu et al., "Asymmetric Synthesis of Enantiomerically Pure (–)–(1'R,4'R)–Dioxolane–thymine and Its Anti–HIV Activity", *Tetrahedron Lett.*, vol. 31, pp. 3791–3794 (1991).

V. Farina et al., "A New Synthesis of 2',3'–Dideoxynucleosides for AIDS Chemotherapy", *Tetrahedron Lett.*, vol. 29, pp. 1239–1242 (1988).

(List continued on next page.)

*Primary Examiner*—John M. Ford
*Assistant Examiner*—Thomas C. McKenzie
(74) *Attorney, Agent, or Firm*—Millen, White, Zelano & Branigan

(57) ABSTRACT

Disclosed are processes for preparing compounds of the formula (I) and pharmaceutically acceptable salts or esters thereof:

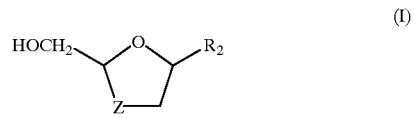

(I)

wherein $R_2$ is a purine or pyrimidine base or an analogue or derivative thereof; and Z is S, S=O or $SO_2$. The invention also relates to intermediates of use in the preparation of these compounds.

22 Claims, No Drawings

OTHER PUBLICATIONS

B. Ganem, "Synthesis of Iso–ddA, Member of Novel Class of Anti–HIV Agents; Dioxolane–T, A New 2',3'–Dideoxynucleoside Prototype with In Vitro Activity Against HIV", *Chemtracts–Organic Chemistry*, vol. 3, pp. 249–251 (1990).

G. Hesse et al., "Mercapto–acetaldehyd und Dioxy–1,4–dithian", *Chem.Ber.*, vol. 85, pp. 924–932 (1952).

D.C. Humber et al., "Expeditious Preparation of (–)–2'–Deoxy–3'–Thiacytidine (3TC)", *Tetrahedron Lett.*, vol. 33, pp. 4625–4628 (1992).

L.S. Jeong, et al., "Asymmetric Synthesis and Biological Evaluation of β–L–(2R,5S)–and α–L–(2R,5R)–,3–Oxathiolane–Pyrimidine and –Purine Nucleosides as Potential Anti–Hiv Agents", *J.Med.Chem.*, vol. 36, pp. 181–195 (1993).

J.L. Kraus, et al., "Synthesis of New 2,5–Disubstituted 1,3–Oxathiolanes. Intermediates in Nucleoside Chemistry", *Synthesis*, pp. 1046–1048 (1991).

H.O. Kim, et al., "Asymmetric Synthesis of 1,3–Dioxolane–Pyrimidine Nucleosides and Their Anti–HIV Activity", *J.Med.Chem.*, vol. 35, pp. 1987–1995 (1992).

J.M. McIntosh et al., "2–Mercaptoaldehyde Dimers and 2,5–Dihydrothiophenes From 1,3–Oxathiolan–5–ones", *Can.J.Chem.*, vol. 61, pp. 1872–1875 (1983).

D.W. Norbeck et al., "(±)–Dioxolane–T ((±)–1–[(2β,4β)–2–(hydroxymethyl)–4–dioxolanyl]thymine) A New 2',3'–Dideoxy–nucleoside Prototype With In Vitro Activity Against HIV", *Tetrahedron Lett.*, vol. 30, pp. 6263–6266 (1989).

M. Okabe et al., "Synthesis of the Dideoxynucleosides ddC and CNT from Glutamic Acid, Ribonolactone, and Pyrimidine Bases", *J.Org.Chem.*, vol. 53, pp. 4780–4786 (1988).

R. Storer et al., "The Resolution And Absolute Stereochemistry of the Enantiomers of cis–1–[2–(Hydroxymethyl)–1,3–Oxathiolan–5–yl] Cytosine (BCH–189): Equipotent Anti–HIV Agents", *Nucleosides & Nucleotides*, vol. 12, pp. 225–236 (1993).

E. Vedejs, et al., "Method for Sulfide S–Benzylation or S–Allylation Using Trimethylsilyl Triflate Activated Benzyl or Allyl Ethers", *J.Org.Chem.*, vol. 46, pp. 3353–3354 (1981).

W–B. Choi, et al., "In Situ Complexation Directs the Stereochemistry of N–Glycoslylation in the Synthesis of Oxathiolanyl and Dioxolanyl Nucleoside Analogues", *J.Am. Chem.Soc.*, vol. 113, pp. 9377–9379 (1991).

W–B. Choi, et al., "Synthesis, Anti–Human Immunodeficiency Virus, and Anti–Hepatitis B Virus Activity of Pyrimidine Oxathiolane Nucleosides", *Bioorg. & Med. Chem. Lett.*, vol. 3(4), pp. 693–696 (1993).

C.K. Chu et al., "Enantiomeric Synthesis of (+)–BCH–189 [(+)–(2S,5R)–1–[2–Hydroxymethyl)–1,3–oxathiolan–5–yl] cytosine] from D–Mannose and Its Anti–HIV Activity", *J.Org.Chem.*, vol. 56, pp. 6503–6505 (1991).

C.A. Evans, et al., "Divergent Asymmetric Synthesis of Dioxolane Nucleoside Analogues", *Tetrahedron Asymmetry*, vol. 4(11), pp. 2319–2322 (1993).

P. Faury, et al., "Synthesis of Tetrazole Oxathiolane Nucleoside Analogues and Their Evaluation as HIV–1 Antiviral Agents", *Nucleosides & Nucleotides*, vol. 11(8), pp. 1481–1488 (1992).

L.S. Jeong, et al., "An Efficient Synthesis of Enantiomerically Pure (+)–(2S,5R)–1–[2–(Hydroxymethyl)–1,3–Oxathiolan–5–yl)cytosine [(+)–BCH–189] from D–Galactose", *Tetrahedron Lett.*, vol. 33, pp. 595–598 (1992).

L.S. Jeong, et al., "Structure–Activity Relationships of β–D–(2S,5R)–and α–D–(2S,5S)–1,3–Oxathiolanyl Nucleosides as Potential Anti–HIV Agents", *J.Med.Chem.*, vol. 36, pp. 2627–2638 (1993).

H. Jin, et al., "Unexpected Effects of Lewis Acids in the Synthesis of Optically Pure 2'–Deoxy–3'Oxayctidine Nucleoside Analogues", *Tetrahedron Asymmetry*, vol. 4(2), pp. 211–214 (1993).

H.O. Kim, et al., "Potent Anti–HIV and Anti–HBV Activities of (–)–L–β–Dioxolane–C and (+)–L–β–Dioxolane–T and Their Asymmetric Syntheses", *Tetrohedron Lett.*, vol. 33, pp. 6899–6902 (1992).

H.O. Kim, et al., "1,3–Dioxolanylpurine Nucleosides (2R, 4R) and (2R,4S) with Selective Anti–HIV–1 Activity in Human Lymphocytes", *J.Med.Chem.*, vol. 36, pp. 30–37 (1993).

M.A. Siddiqui, et al., "Antiviral Optically Pure Dioxolane Purine Nucleosides Analogues", *Bioorg. & Med. Chem. Lett.*, vol. 3(8), pp. 1543–1546 (1993).

L.J. Wilson, et al., "The Synthesis and Anti–HIV Activity of Pyrimidine Dioxolanyl Nucleosides", *Bioorg. & Med. Chem. Lett.*, vol. 3(2), pp. 169–174 (1993).

\* cited by examiner

PROCESSES FOR PREPARING SUBSTITUTED 1,3-OXATHIOLANES WITH ANTIVIRAL PROPERTIES

CROSS-REFERENCE TO RELATED APPLICATIONS

This application is a divisional of application Ser. No. 08/040,163, filed Mar. 29, 1993, now U.S. Pat. No. 5,466,806, which is a continuation-in-part of application Ser. No. 07/564,160, filed Aug. 7, 1990, now abandoned, which is a continuation-in-part of application Ser. No. 07/308,101, filed Feb. 8, 1989, now U.S. Pat. No. 5,047,407, and U.S. Ser. No. 07/546,676, filed Jun. 29, 1990, now U.S. Pat. No. 5,041,449, which is a continuation of application Ser. No. 07/179,615, filed Apr. 11, 1988, now abandoned.

The present invention relates to processes for preparing substituted 1,3-oxathiolanes with antiviral activity and intermediates of use in their preparation.

BACKGROUND OF THE INVENTION

Nucleosides, and in particular, 1,3-oxathiolanes and their analogues and derivatives are an important class of therapeutic agents. For example, a number of nucleosides have shown antiviral activity against retroviruses such as human immunodeficiency viruses (HIV), hepatitis B virus (HBV) and human T-lymphotropic virus (HTLV).

The most potent anti-HIV compounds thus far reported are 2',3'-dideoxynucleosides, more particularly, 2',3'-dideoxycytidine (ddC) and 3'-azido-2',3'-dideoxythymidine (AZT). These compounds are also active against other kinds of retroviruses such as the Moloney murine leukemia virus. However, clinically, both compounds are toxic.

A structurally distinct class of compounds known as 2-substituted-5-substituted-1,3-oxathiolanes has been found to have superior antiviral and antiretroviral activity without cell toxicity. See, e.g., EP 0382526A and WO 91/17159 the disclosures of which are incorporated herein by reference.

Because of the increasing incidence and the life-threatening characteristics of AIDS, there is a great need to develop a general synthetic scheme for substituted 1,3-oxathiolanes which is efficient, amenable to large scale, inexpensive and based on readily available starting material. It is therefore an advantage of the present invention to provide synthesis of substituted 1,3-oxathiolanes that is readily feasible.

DESCRIPTION OF THE INVENTION

The processes of this invention may be used to prepare the compounds of formula (I) and pharmaceutically acceptable salts or esters thereof:

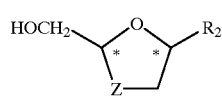

(I)

wherein $R_2$ is a purine or pyrimidine base or an analogue or derivative thereof; and Z is S, S=O or $SO_2$.

It will be appreciated by those skilled in the art that the compounds of formula (I) contain at least two chiral centers (shown as * in formula (I)) and thus exist in the form of two pairs of optical isomers (i.e., enantiomers) and mixtures thereof including racemic mixtures. Thus the compounds of formula (I) may be either cis isomers, as represented by formula (II), or trans isomers, as represented by formula (III), or mixtures thereof. Each of the cis and trans isomers can exist as one of two enantiomers or as mixtures thereof including racemic mixtures. The preparation of all such isomers and mixtures thereof including racemic mixtures is included within the scope of the invention.

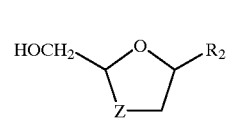

(II)

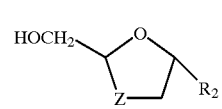

(III)

It will also be appreciated that when Z is S=O the compounds exist in two additional isomeric forms as shown in formulas (IIa) and (IIb) which differ in the configuration of the oxide oxygen atom relative to the 2,5-substituents. The processes of this invention additionally embrace the preparation of such isomers and mixtures thereof.

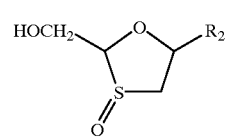

(IIa)

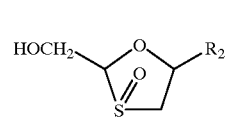

(IIb)

The purine or pyrimidine base or analogue or derivative thereof $R_2$ will be linked at any position of the base, preferably at the N9- or N1-position, respectively.

By "purine or pyrimidine base" or an analogue or derivative thereof is meant a purine or pyrimidine base found in native nucleosides or an analogue thereof which mimics such bases in that their structures (the kinds of atoms and their arrangement) are similar to the native bases but may either possess additional or lack certain of the functional properties of the native bases. Such analogues include those derived by replacement of a $CH_2$ moiety by a nitrogen atom (for example, 5-azapyrimidines such as 5-azacytosine) or vice verse (for example 7-deazapurines, for example 7-deazaadenosine or 7-deazaguanosine) or both (e.g., 7-deaza-8-azapurines). By derivatives of such bases or analogues are meant those compounds wherein ring substituents are either incorporated, removed or modified by conventional substituents known in the art, e.g., halogen, hydroxyl, amino, $C_{1-6}$ alkyl. Such purine or pyrimidine bases, analogues and derivatives will be well known to those skilled in the art.

Preferably the group $R_2$ is selected from:

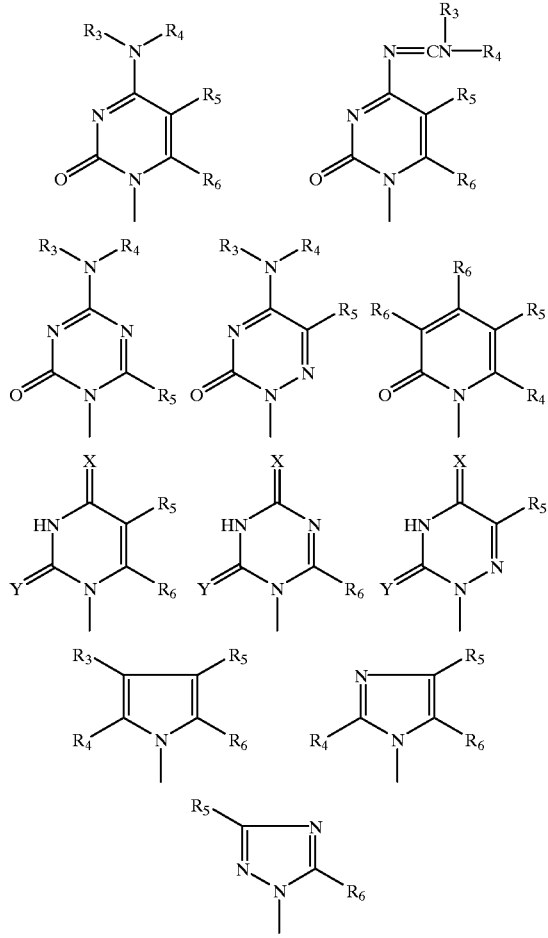

wherein:

X is oxygen or sulfur; Y is oxygen or sulfur;

$R_3$ and $R_4$ are independently selected from the group consisting of hydrogen, hydroxyl, amino, substituted or unsubstituted $C_{1-6}$ alkyl, or $C_{1-6}$ alkenyl or $C_{1-6}$ alkynyl, and substituted or unsubstituted Cl-lo acyl or aracyl;

$R_5$ and $R_6$ are independently selected from the group consisting of hydrogen, halogen, hydroxyl, amino, cyano, carboxy, carbamoyl, alkoxycarbonyl, hydroxymethyl, trifluoromethyl, thioaryl, substituted or unsubstituted $C_{1-6}$ alkyl or $C_{1-6}$ alkenyl or $C_{1-6}$ alkynyl, and substituted or unsubstituted $C_{1-10}$ acyloxy;

and

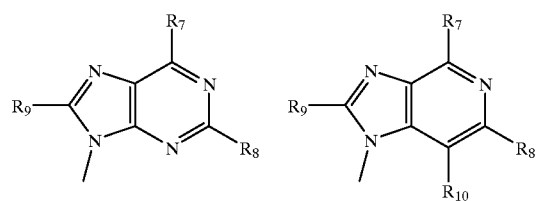

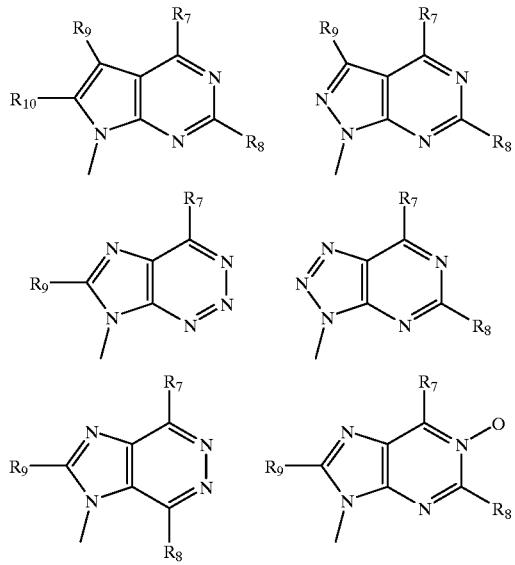

wherein:

$R_7$ and $R_8$ are independently selected from the group consisting of hydrogen, hydroxy, alkoxy, thiol, thioalkyl, amino, substituted amino, halogen, cyano, carboxy, alkoxycarbonyl, carbamoyl, substituted or unsubstituted $C_{1-6}$ alkyl, or alkenyl, or alkynyl, and substituted or unsubstituted $C_{1-10}$ acyloxy; and $R_9$ and $R_{10}$ are independently selected from the group consisting of hydrogen, hydroxyl, alkoxy, amino, substituted amino, halogen, azido, substituted or unsubstituted $C_{1-6}$ alkyl or alkenyl or alkynyl, and substituted or unsubstituted $C_{1-10}$ acyloxy.

More preferably, the $R_2$ group is selected from:

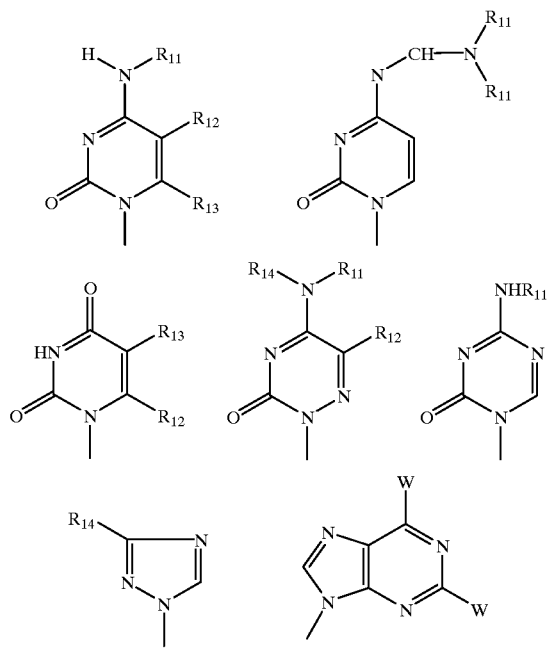

-continued

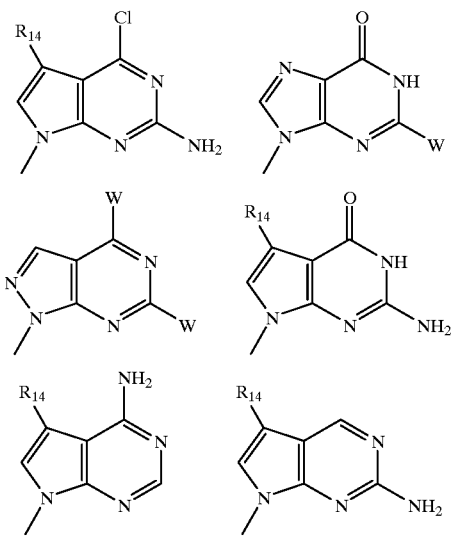

wherein each $R_{11}$ is independently selected from hydrogen, acetyl, and $C_{1-6}$ alkyl groups;

$R_{12}$ and $R_{13}$ are independently selected from hydrogen, hydroxymethyl, trifluoromethyl, substituted or unsubstituted $C_{1-6}$ alkyl or alkenyl, bromine, chlorine, fluorine, and iodine;

$R_{14}$ is selected from hydrogen, cyano, carboxy, ethoxycarbonyl, carbamoyl, and thiocarbamoyl; and each W is independently selected from hydrogen, bromine, chlorine, fluorine, iodine, amino, and hydroxyl groups.

Most preferably $R_2$ is

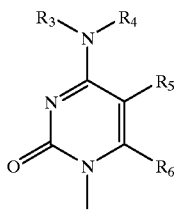

wherein $R_3$ and $R_6$ are hydrogen, and $R_4$ and $R_5$ are as defined above.

Z is preferably —S—.

By "a pharmaceutically acceptable salt or ester" is meant any pharmaceutically acceptable salt, ester, or salt of such ester, of a compound of formula (I) or any other compound which, upon administration to the recipient, is capable of providing (directly or indirectly) a compound of formula (I) or an antivirally active metabolite or residue thereof.

It will be appreciated by those skilled in the art that the compounds of formula (I) may be modified to provide pharmaceutically acceptable derivatives thereof, at functional groups in both the base moiety, $R_2$, and at the hydroxymethyl group of the oxathiolane ring. Modification at all such functional groups is included within the scope of the processes of this invention. However, of particular interest are pharmaceutically acceptable derivatives (e.g., esters) obtained by modification of the 2-hydroxymethyl group of the oxathiolane ring.

Preferred esters of the compounds of formula (I) produced by the process of this invention include the compounds in which OH is replaced by a carboxyl function R(CO)O— in which the non-carbonyl moiety R is selected from hydrogen, straight or branched chain alkyl (e.g. methyl, ethyl, n-propyl, t-butyl, n-butyl), alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy), substituted dihydropyridinyl (e.g. N-methyldihydropyridinyl). The OH function may also be replaced by sulphonate esters such as alkyl-or aralkylsulphonyl (e.g. methanesulphonyl), sulfate esters, amino acid esters (e.g. L-valyl or L-isoleucyl), or mono-, di- or tri-phosphate esters. Also included within the scope of such esters are esters derived from polyfunctional acids such as carboxylic acids containing more than one carboxyl group, for example, dicarboxylic acids $HOOC(CH_2)_qCOOH$ where q is an integer of 0 to 10 (for example, succinic acid) or phosphoric acids. Methods for preparing such esters are well known. See, for example, Hahn et al., "Nucleotide Dimers as anti-Human Immunodeficiency Virus Agents", *Nucleotide Analogues*, pp. 156–159 (1989) and Busso et al., "Nucleotide Dimers Supress HIV Expression In Vitro", *AIDS Research and Human Retroviruses*, 4(6), pp.449–455 (1988). Where esters are derived from such acids, each acidic group is preferably esterified by a compound of formula (I) or other nucleoside or analogs and derivatives thereof to provide esters of the formula:

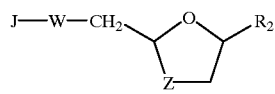

(IV)

where W is —OC—$(CH_2)_n$—CO— where n is an integer of 0 to 10, a phosphate group, or a thiophosphate group, Z and $R_2$ are as defined above, and J is any nucleoside or nucleoside analog or derivative thereof.

Among the preferred nucleosides and nucleoside analogs are 3'-azido-2',3'-dideoxythymidine; 2',3'-dideoxycytidine; 21,3'-dideoxyadenosine; 2',3'-dideoxyinosine; 2',3'-dideoxythymidine; 2',3'-dideoxy-2',3'-didehydrothymidine; 2',3'-dideoxy-2',3'-didehydrocytidine and ribavirin and those nucleosides whose bases are depicted on pages 4–5 of this specification. The most preferred nucleoside or nucleoside analog is chosen among the compounds of formula (I) to form a homodimer consisting of two nucleosides of formula (I).

With regard to the above described esters, unless otherwise specified, any alkyl moiety present advantageously contains 1 to 16 carbon atoms, preferably 1 to 4 carbon atoms and could contain one or more double bonds. Any aryl moiety present in such esters advantageously comprises a phenyl group.

In particular, the esters may be a $C_{1-16}$ alkyl ester, an unsubstituted benzoyl ester or a benzoyl esters substituted by at least one halogen (bromine, chlorine, fluorine or iodine), $C_{1-6}$ alkyl or alkenyl, saturated or unsaturated $C_{1-6}$ alkoxy, nitro or trifluoromethyl groups.

Pharmaceutically acceptable salts of the compounds of formula (I) include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicylic, succinic, p-toluenesulfonic, tartaric, acetic, citric, methanesulfonic, formic, benzoic, malonic, naphthalene-2-sulfonic, and benzenesulfonic acids.

Other acids such as oxalic, while not in themselves pharmaceutically acceptable, may be useful in the preparation of salts useful as intermediates in obtaining the compounds of the invention and their pharmaceutically acceptable acid addition salts.

Salts derived from appropriate bases include alkali metal (e.g. sodium), aLkaline earth metal (e.g. magnesium), ammonium and $N(R')_4^+$ (where R' is $C_{1-4}$ alkyl) salts.

In the processes for preparing the compounds of this invention, the following definitions are used:

$R_1$ is a hydroxyl protecting function such as an acyl having from 1 to 16 carbon atoms unsubstituted or substituted with a heteroatom (e.g. benzoyl), or a silyl function such as trialkylsilyl (e.g. t-butyldimethylsilyl);

$R_2$ is a purine or pyrimidine base or an analogue or derivative thereof;

$R_w$ is hydrogen or $R_1$;

$R_x$ is a substituted or unsubstituted $C_{1-6}$ alkyl;

$R_y$ is a substituted or unsubstituted $C_{1-12}$ alkyl or substituted or unsubstituted $C_{6-20}$ aryl; and L is a leaving group.

As used in the processes of this invention, a "leaving group" is an atom or group which is displaceable upon reaction with an appropriate base, with or without a Lewis acid. Suitable leaving groups include alkoxy carbonyl groups such as ethoxy carbonyl; halogens such as iodine, bromine or chlorine, fluorine; substituted or unsubstituted saturated or unsaturated thiolates, such as thiomethyl or thiophenyl; substituted or unsubstituted saturated or unsaturated selenino compounds, such as phenyl selenide or alkyl selenide; substituted or unsubstituted saturated or unsaturated aliphatic or aromatic ketones such as methyl ketone; or —$OR_z$ where $R_z$ is hydrogen or a substituted or unsubstituted saturated or unsaturated alkyl group, e.g., a $C_{1-6}$ alkyl or alkenyl group such as methyl; a substituted or unsubstituted aliphatic or aromatic acyl group, e.g., a $C_{1-6}$ aliphatic acyl group such as acetyl and an aromatic acyl group such as benzoyl; a substituted or unsubstituted saturated or unsaturated alkoxy carbonyl group, such as methyl carbonate and phenyl carbonate; substituted or unsubstituted sulphonyl imidazolide; substituted or unsubstituted carbonyl imidazolide; substituted or unsubstituted aliphatic or aromatic amino carbonyl group, such as phenyl carbamate; substituted or unsubstituted alkyl imidate group such as trichloroacetamidate; substituted or unsubstituted saturated or unsaturated phosphinoyl, such as diethylphosphinoyl; substituted or unsubstituted aliphatic or aromatic sulphonyl group, such as tosylate.

One process according to the invention is illustrated in SCHEME 1. The process of SCHEME 1 is further illustrated using specific reagents and compounds in SCHEMES 1A and 1B.

The various steps involved in the synthesis as illustrated in SCHEME 1 may be briefly described as follows:

Step 1: A mercaptoacetaldehyde monomer produced from the dimer in a suitable solvent is reacted directly with any aldehyde of the formula $R_wOCH_2CHO$ (VII) to yield an oxathiolane lactol of formula (XIII).

The glycoaldehyde derivative of formula (VII) may be generated from the dimer by any means known in the art as depicted in SCHEME 1B.

Step 2: The hydroxyl group of the compound of formula (XIII) is converted to a leaving group with a suitable reagent in a compatible organic solvent to yield an important oxathiolane intermediate of formula (XIV).

Step 3: The oxathiolane intermediate of formula (XIV) is reacted with a previously silylated purine or pyrimidine base to give a purin-9'-yl or pyrimidin-1'-yl substituted oxathiolane of formula (IX) where Z is sulfur.

Optionally, the sulfur may be oxidized at this stage or at any other following stage to obtain compounds where Z is S=O or $SO_2$.

Step 4: The base $R_2$ shown in formula (IX) is acylated in a suitable solvent to yield a compound of formula (X) where $R_2'$ is acylated-$R_2$ which provides for easier separation of isomers.

Therefore, at this stage, the compound of formula (X) is optionally separated to its cis or trans isomer.

Step 5: The acyl functionalities of $R_2'$ and $R_1COOCH_2$ of compound of formula (X) are hydrolyzed under basic conditions (sequentially or at the same time) to yield an oxathiolane of formula (I).

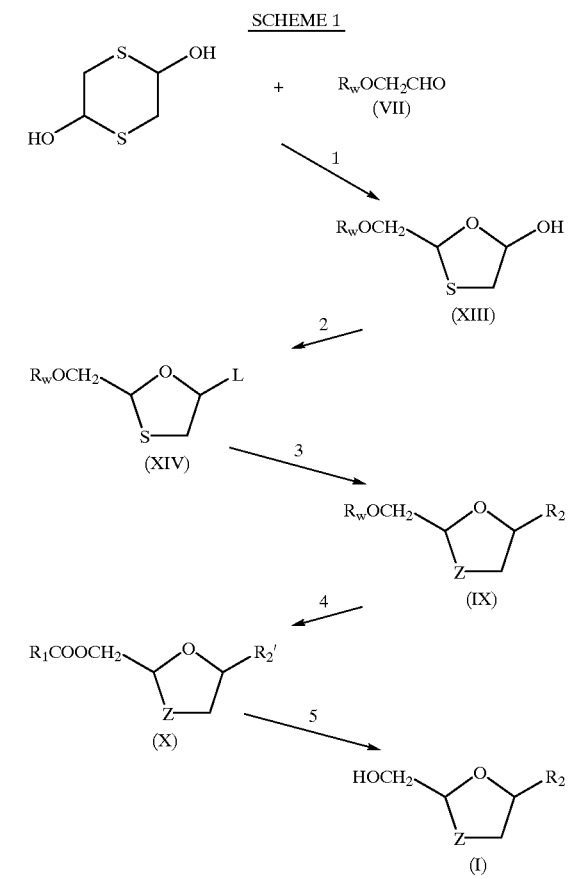

SCHEME 1

SCHEME 1A

Step 1: A mercaptoacetaldehyde monomer produced from the dimer in pyridine is reacted directly with benzoyloxyacetaldehyde (VII-A) to yield an oxathiolane lactol of formula (XIII-A).

Step 2: The hydroxyl group of the compound of formula (XIII-A) is converted to a leaving group with acetyl chloride in a compatible organic solvent, such as dichloromethane or chloroform, to yield intermediate of formula (XIV-A).

Step 3: The oxathiolane intermediate of formula (XIV-A) is reacted with a previously silylated cytosine to give a cytosin-1'-yl oxathiolane of formula (IX-A).

Step 4: The amine function of the base in compound of formula (IX-A) is acylated with acetic anhydride in pyridine to yield a compound of formula (X-A) which provides for easier separation of isomers.

Step 5: The acyl functions of the compound of formula (X-A) are hydrolyzed with ammonia in methanol to yield an oxathiolane of formula (I-A).

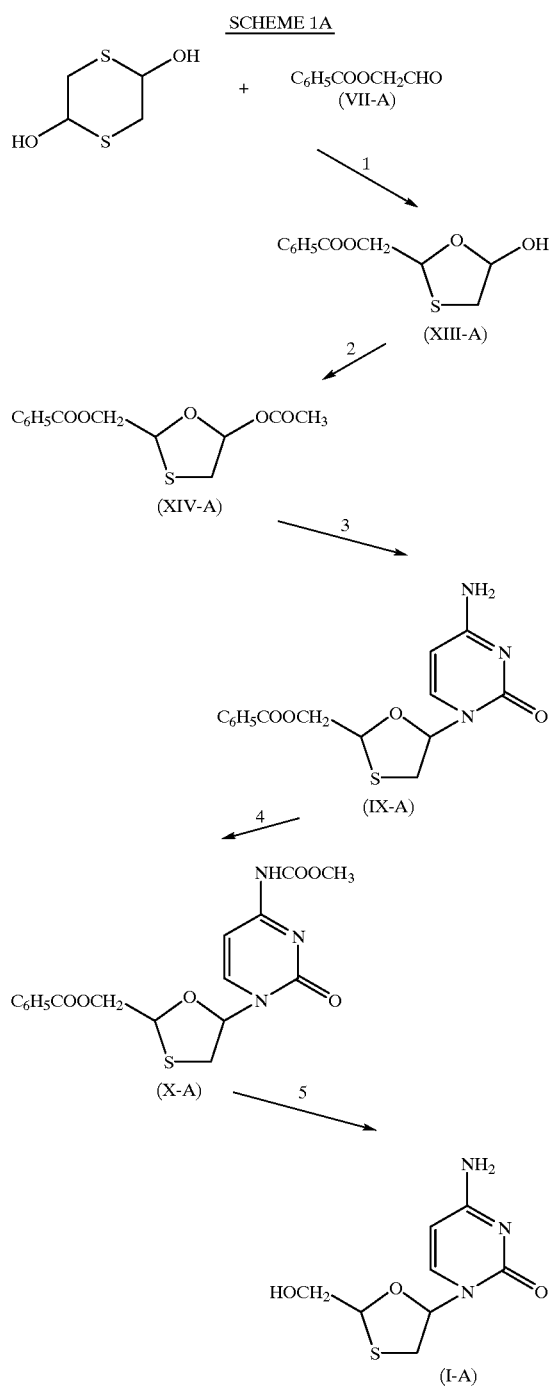

SCHEME 1B

The glycoaldehyde dimer (VII-B) is used as a source of the glycoaldehyde.

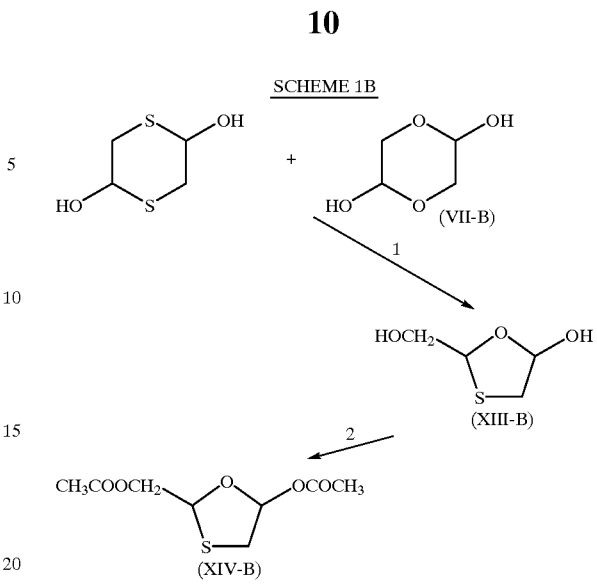

A second and preferred process for producing oxathiolane compounds is illustrated in SCHEME 2. This process is further illustrated using specific reagents and compounds in SCHEME 2A.

The various steps involved in the synthesis as illustrated in SCHEME 2 may be briefly described as follows:

Step 1: Mercaptoacetaldehyde monomer produced from the dimer in a suitable solvent is reacted directly with any organic glyoxylate of the formula RyOOCCHO to yield an oxathiolane lactol of formula (XV).

Step 2: The hydroxyl group of the compound of formula (XV) is converted to a leaving group with a suitable reagent in a compatible organic solvent to yield an important oxathiolane intermediate of formula (XVI).

Step 3: The oxathiolane intermediate of formula (XVI) is reacted with a previously silylated purine or pyrimidine base, in the presence of a Lewis acid, to give purin-9'-yl or pyrimidin-1'-yl substituted oxathiolane of formula (XVII) where Z is S, predominantly as the cis-isomer.

Optionally, the sulfur may be oxidized at this stage or at any other following stage to give compounds where Z is $S=O$ or $SO_2$.

Step 4: The ester group of the oxathiolane of formula (XVII) is selectively reduced with a suitable reducing agent in a compatible organic solvent to yield an oxathiolane nucleoside of formula (XVIII).

At this stage, the compound of formula (XVIII) is optionally separated to its cis and trans isomers.

Step 5: The hydroxyl group of the compound of formula (XVIII) is protected with a suitable silyl protecting group in an appropriate solvent to yield an oxathiolane of formula (XIX).

Step 6: The $R_2$ base of formula (XIX-A) can be interconverted to another base $R_{2a}$ by reaction with a suitable reagent to yield an oxathiolane of formula (XX).

Step 7: The protecting group $R_1$ of the compound of formula (XX) is removed under neutral conditions using a suitable reagent in a suitable solvent to yield the oxathiolane of formula (I).

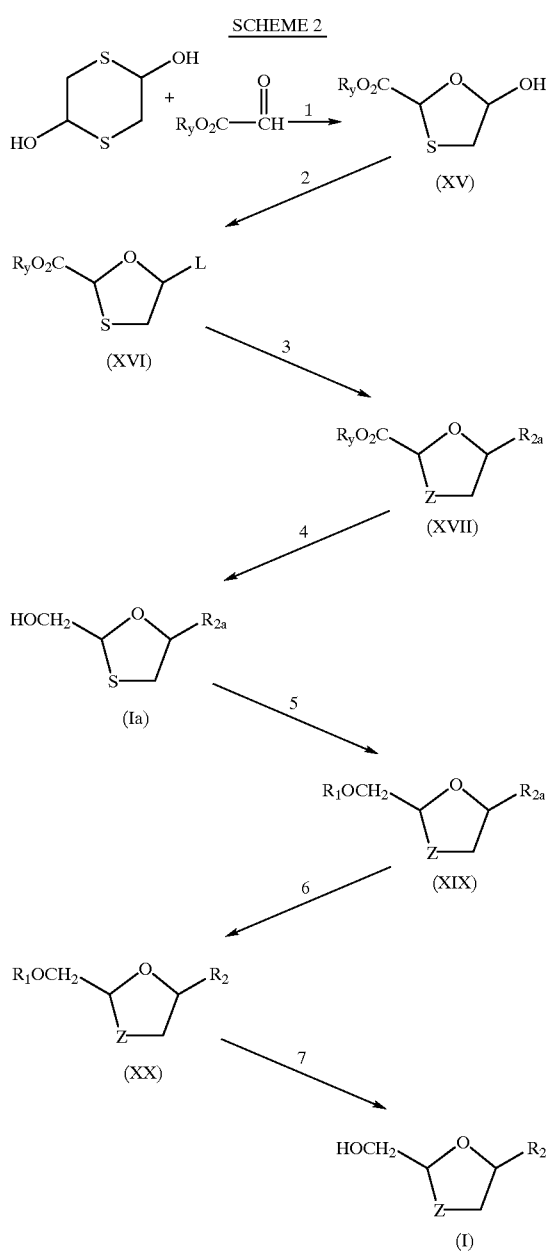

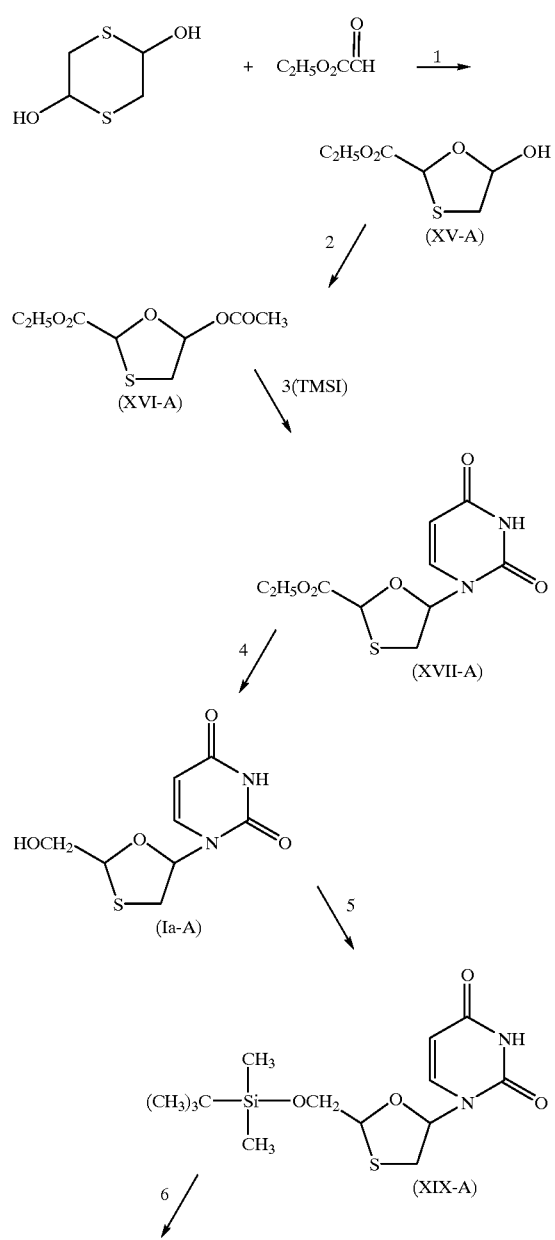

Step 5: The hydroxyl group of the compound of formula (XVIII-A) is protected with t-butyldimethyl silyl in dimethylformamide (DMF) to yield an oxathiolane of formula (XIX-A).

Step 6: The uracil base of formula (XIX-A) can be interconverted to cytosine, by reaction with p-chlorophenoxy phosphorous oxychloride followed by amination with ammonia in methanol to yield an oxathiolane of formula (XX-A).

Step 7: The silyl group of the compound of formula (XX-A) is removed under neutral conditions using tetra n-butyl ammonium fluoride in tetrahydrofuran to yield the oxathiolane of formula (I).

SCHEME 2A
Step 1: Mercaptoacetaldehyde dimer in pyridine is reacted directly with ethyl glyoxylate to yield an oxathiolane lactol of formula (XV-A).
Step 2: The hydroxyl group of the compound of formula (XV-A) is converted to an acetyl leaving group with acetyl chloride in a compatible organic solvent such as dichloromethane, chloroform or pyridine, to yield intermediate of formula (XVI-A).
Step 3: The oxathiolane intermediate of formula (XVI-A) is reacted with previously silylated uracil, in the presence of trimethylsilyl iodide, to give uracil-1'-yl oxathiolane of formula (XVII-A), predominantly as the cis-isomer.
Step 4: The ester group of the oxathiolane of formula (XVII-A) is selectively reduced with sodium borohydride in methanol to yield an oxathiolane nucleoside of formula (XVIII-A).

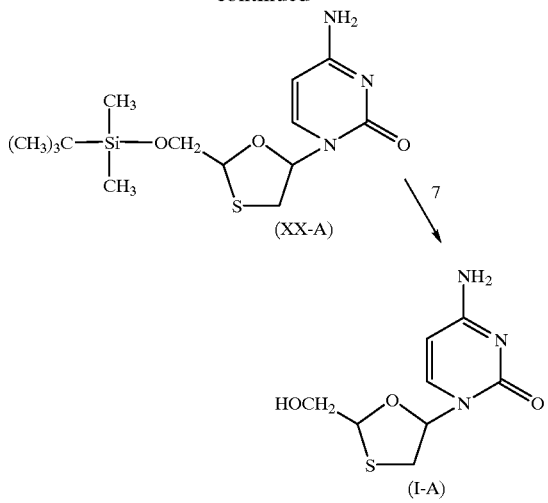

Although the process of Scheme 2 generally provides nucleoside analogues predominantly in their cis form, such a process is most preferred for pyrimidine bases because of high cis-selectivity.

For purines, although the process of Scheme 2 does yield more cis isomer than trans, the ratio obtained is moderate. An alternative process has been designed to obtain purin-yl nucleosides in high cis:trans ratios.

Briefly, steps 1 and 2 of Scheme 2 remain the same. However, the coupling procedure (step 3) between the compound of formula (XVI) and the base (preferably purine) is modified as follows:

Step 3a: The oxathiolane intermediate of formula (XVI) is reacted with a halogen-containing silyl Lewis acid such as trimethylsilyl iodide, to give an intermediate of formula (XXVI):

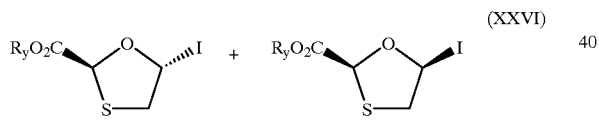

Step 3b: The intermediate of formula (XXVI) is then mixed with a base (preferably a purine) under basic conditions to yield the intermediate of formula (XVII) predominantly as the cis isomer.

As an alternative to process 2, a third process according to this invention for producing oxathiolane compounds is illustrated in SCHEME 3. This process is illustrated using specific reagents and compounds, for example, in SCHEME 3A.

The various steps involved in the synthesis as illustrated in SCHEME 3 may be briefly described as follows:

Step 1: Similar to SCHEME 2.
Step 2: The hydroxyl group of the intermediate of formula (XV), is converted to a leaving group with a suitable reagent in a compatible organic solvent to yield an important intermediate of formula (XXI).
Step 3: The ester group of the intermediate of formula (XXI) is selectively reduced with a suitable reducing agent in a compatible organic solvent and the resultant hydroxyl group is directly protected with a suitable group $R_1$ to yield an oxathiolane of formula (XXII).
Step 4: The oxathiolane of formula (XXII) is reacted with previously silylated purine or pyrimidine base in the presence of a Lewis Acid to give a pyrimidin-1'-yl or purin-9'-yl oxathiolane of formula (XXIII) where Z is S (optionally oxidized to S=O or $SO_2$).
Step 5: The base $R_2$ shown in formula (XXIII) is acylated with acetic anhydride in a solvent to yield a compound of formula (XXIV) where $R_2'$ is an acylated $R_2$ which provides for easier separation of isomers.

Therefore, at this stage, the compound of formula (X) is optionally separated to its cis or trans isomer.

Step 6: The acetyl functionality of $R_2'$ of the compound of formula (XXIV) is hydrolyzed under basic conditions to yield an oxathiolane of formula (XXV).
Step 7: Removal of the $R_1$ protecting group is effected by suitable reagents in a compatible solvent to yield an oxathiolane of formula (I).

SCHEME 3

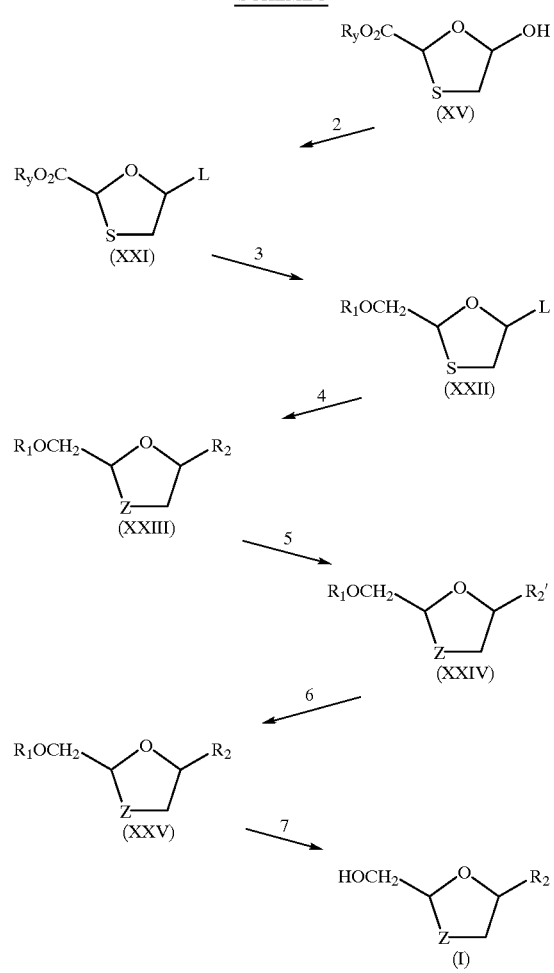

SCHEME 3A

Step 2: The hydroxyl group of the intermediate of formula (XV-A), is converted to a carbonate leaving group with methyl chloroformate in a compatible organic solvent to yield an intermediate of formula (XXI-A).
Step 3: The ester group of the intermediate of formula (XXI-A) is selectively reduced with sodium borohydride in methanol and the resultant hydroxyl group is directly protected with t-butyldiphenylsilyl to yield an oxathiolane of formula (XXII-A).
Step 4: The oxathiolane of formula (XXII-A) is reacted with previously silylated cytosine, in the presence of trimethylsilyltriflate or iodotrimethylsilane, to give cytosin-1'-yl oxathiolane of formula (XXIII-A).

Step 5: The amine function of the cytosine of compound (XXIII-A) is acylated with acetic anhydride in pyridine to yield a compound of formula (XXIV-A) so that the cis- and trans-isomers may be separated.

Step 6: The acetyl functionality of the compound of formula (XXIV-A) is hydrolyzed under basic conditions to yield an oxathiolane of formula (XXV-A).

Step 7: Removal of the silyl group is effected by using tetra-n-butylammonium fluoride in tetrahydrofuran yield an oxathiolane of formula (I).

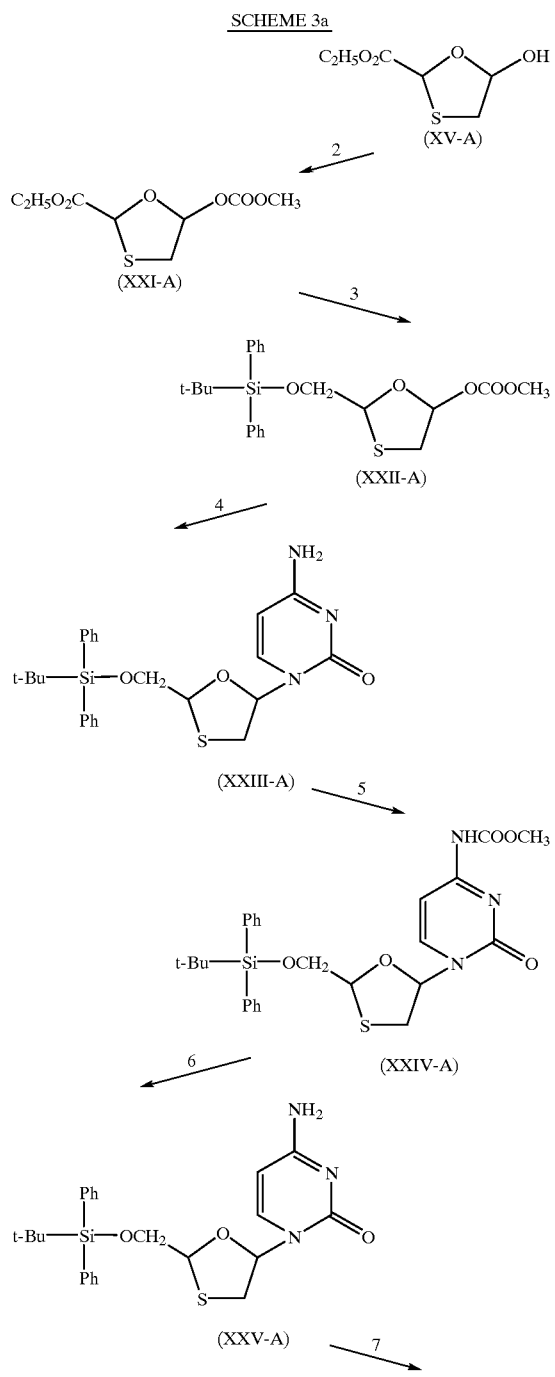

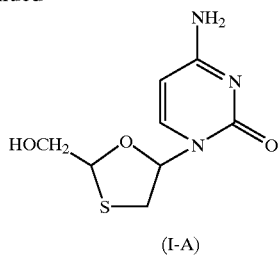

In the proccesses of this invention, the following intermediates are of partivular impoerance:

trans-2-hydtoxymethyl-5-acetoxy-1,3-oxathiolane cis-2-benzoyloxymethyl-5-hydroxy-1,3-oxathiolane, trans-2-benzoyloxymethyl-5-hydtoxy-1,3-oxathiolane and mixture thereof;

cis-2-benzoyloxymethyl-5-(4',5'-dichlorobenzoyloxy)-1,3-oxathiolane, tran-2-benzoyloxmethyl-5-(4',5'-dichlorobenzoyloxy)-1,3-oxathiolane and mixtures thereof;

cis-2-benzoyloxymethyl-5-trimethylacetoxy-1,3-oxathiolane, trans-2-benzoyloxymethyl-5-trimethylacetoxy-1,3-oxathiolane and mixtures thereof;

cis-2-benzoyloxymethyl-5-(2',2',2'-trichloroethoxycarbonyloxy)1,3-oxathiolane, trans-2-benzoyloxymethyl-5-(2',2',2'-trichloroethoxycarbonyloxy)1,3-oxathiolane and mixtures thereof;

cis-2-benzoyloxymethyl-5-ethoxycarbonyloxy-1,3-oxathiolane, trans-2-benzoyloxymethyl-5-ethoxycarbonyloxy-1,3-oxathiolane and mixtures thereof;

cis-2-benzoyloxymethyl-5-methoxycarbonyloxy-1,3-oxathiolane, trans-2-benzoyloxymethyl-5-methoxycarbonyloxy-1,3-oxathiolane and mixtures thereof;

cis-2-benzoyloxymethyl-5-acetoxy-1,3-oxathiolane, trans-2-benzoyloxymethyl-5-acetoxy-1,3-oxathiolane and mixtures thereof;

cis-2-benzoyloxymethyl-5-(N4'-acetylcytosin-1'-yl)-1,3-oxathiolane, trans-2-benzoyloxymethyl-5-(N4'-acetylcytosin-1'-yl)-1,3-oxathiolane and mixtures thereof;

cis-2-benzoyloxymethyl-5-(cytosin-1'-yl)-1,3-oxathiolane, trans-2-benzoyloxymethyl-5-(cytosin-1'-yl)-1,3-oxathiolane and mixtures thereof;

cis-2-carboethoxy-5-hydroxy-1,3-oxathiolane, trans-2-carboethoxy-5-hydroxy-1,3-oxathiolane and mixtures thereof;

cis-2-carboethoxy-5-methoxycarbonyloxy-1,3-oxathiolane, trans-2-carboethoxy-5-methoxycarbonyloxy-1,3-oxathiolane and mixtures thereof;

cis-2-carboethoxy-5-acetoxy-1,3-oxathiolane, trans-2-carboethoxy-5-acetoxy-1,3-oxathiolane and mixtures thereof;

cis-2-carboethoxy-5-(N4'-acetylcytosin-1'-yl)-1,3-oxathiolane;

cis-2-carboethoxy-5-(cytosin-1'-yl)-1,3-oxathiolane;

cis-2-carboethoxy-5-(uracil-1'-yl)-1,3-oxathiolane;

cis-2-benzoyloxymethyl-5-(cytosin-1'-yl)-1,3-oxathiolane;

cis-ethyl-5-iodo-1,3-oxathiolan-2-carboxylate, trans-ethyl-5-iodo-1,3-oxathiolan-2-carboxylate and mixtures thereof;

cis-ethyl-5-(6'-chloropurin-9'-yl)-1,3-oxathiolan-2-carboxylate, trans-ethyl-5-(6'-chloropurin-9'-yl)-1,3-oxathiolan-2-carboxylate and mixtures thereof; and cis-ethyl-5-(6'-chloropurin-7'-yl)-1,3-oxathiolan-2-carboxylate, trans-ethyl-5-(6'-chloropurin-7'-yl)-1,3-oxathiolan-2-carboxylate and mixtures thereof.

Some of the steps described hereinabove have been reported in the context of purine nucleoside synthesis, for example, in "Nucleoside Analogues—Chemistry, Biology and Medical Applications", R. T. Walker et al., Eds, Plenum Press, New York (1979) at pages 193–223, the text of which is incorporated herein by reference.

It will be appreciated that the reactions of the above described processes may require the use of, or conveniently may be applied to, starting materials having protected functional groups, and deprotection might thus be required as an intermediate or final step to yield the desired compound. Protection and deprotection of functional groups may be effected using conventional means. Thus, for example, amino groups may be protected by a group selected from aralkyl (e.g., benzyl), acyl or aryl (e.g., 2,4-dinitrophenyl); subsequent removal of the protecting group being effected when desired by hydrolysis or hydrogenolysis as appropriate using standard conditions. Hydroxyl groups may be protected using any conventional hydroxyl protecting group, for example, as described in "Protective Groups in Organic Chemistry", Ed. J. F. W. McOmie (Plenum Press, 1973) or "Protective Groups in Organic Synthesis" by Theodora W. Greene (John Wiley and Sons, 1991). Examples of suitable hydroxyl protecting groups include groups selected from aralkyl (e.g., benzyl, diphenylmethyl or triphenylmethyl), heterocyclic groups such as tetrahydropyranyl, acyl, (e.g., acetyl or benzoyl) and silyl groups such as trialkylsilyl (e.g., t-butyldimethylsilyl). The hydroxyl protecting groups may be removed by conventional techniques. Thus, for example, alkyl, silyl, acyl and heterocyclic groups may be removed by solvolysis, e.g., by hydrolysis under acidic or basic conditions. Aralkyl groups such as triphenylmethyl may similarly be removed by solvolysis, e.g., by hydrolysis under acidic conditions. Aralkyl groups such as benzyl may be cleaved, for example, by hydrogenolysis. Silyl groups may also conveniently be removed using a source of fluoride ions such as tetra-n-butylammonium fluoride.

In the above processes the compounds of formula (I) are generally obtained as a mixture of the cis and trans isomers. However, in the process depicted in Scheme 2, the ratio of cis:trans may approach 15:1 for pyrimidines, whereas it may approach 10:1 for the purines in the case of the modified process of Scheme 2.

These isomers may be separated, for example, by acetylation, e.g., with acetic anhydride followed by separation by physical means, e.g., chromatography on silica gel and deacetylation, e.g., with methanolic ammonia or by fractional crystallization.

Pharmaceutically acceptable salts of the compounds of the invention may be prepared as described in U.S. Pat. No. 4,383,114, the disclosure of which is incorporated by reference herein. Thus, for example, when it is desired to prepare an acid addition salt of a compound of formula (I), the product of any of the above procedures may be converted into a salt by treatment of the resulting free base with a suitable acid using conventional methods.

Pharmaceutically acceptable acid addition salts may be prepared by reacting the free base with an appropriate acid optionally in the presence of a suitable solvent such as an ester (e.g., ethyl acetate) or an alcohol (e.g., methanol, ethanol or isopropanol). Inorganic basic salts may be prepared by reacting the free base with a suitable base such as an alkoxide (e.g., sodium methoxide) optionally in the presence of a solvent such as an alcohol (e.g., methanol). Pharmaceutically acceptable salts may also be prepared from other salts, including other pharmaceutically acceptable salts, of the compounds of formula (I) using conventional methods.

A compound of formula (I) may be converted into a pharmaceutically acceptable phosphate or other ester by reaction with a phosphorylating agent, such as $POCl_3$, or a suitable esterifying agent, such as an acid halide or anhydride, as appropriate. An ester or salt of a compound of formula (I) may be converted to the parent compound, for example, by hydrolysis.

Where the compound of formula (I) is desired as a single isomer it may be obtained either by resolution of the final product or by stereospecific synthesis from isomerically pure starting material or any convenient intermediate.

Resolution of the final product, or an intermediate or starting material therefore may be effected by any suitable method known in the art: see for example, *Stereochemistry of Carbon Compounds*, by E. L. Eliel (McGraw Hill, 1962) and *Tables of Resolvinc Agents*, by S. H. Wilen.

The invention will be further described by the following examples which are not intended to limit the invention in any way. All temperatures are in degrees celsius.

Examples 1 to 7, and 19 to 23 relate to the process as depicted in Scheme 1. Examples 8 to 10, and 13 to 18 relate to the process as depicted in Scheme 2, and Examples 11, 12, and 19 to 21 relate to the process as depicted in Scheme 3. Examples 24 and 25 relate to the modified process as depicted in Scheme 2 (preferably for purines) and summarized on page 20 of this application.

EXAMPLES

Example 1

CIS AND TRANS 2-BENZOYLOXYMETHYL-5-HYDROXY-1,3-OXATHIOLANE

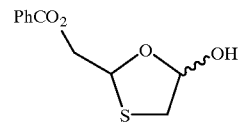

A solution of 216.33 g (1.32 mol) of benzoyloxyacetaldehyde and 100.31 g (0.66 mol) of 1,4-dithiane-2,5-diol in 373 ml (4.61 mol) of pyridine was heated at 60–65° C. under nitrogen atmosphere for 1 hour until all solids dissolved. After cooling, pyridine was removed by distillation and the residue was purified on a silica gel column using EtOAc:hexanes (1:2) as eluent to give 268.5 g of the title compounds (2:1 trans:cis);

$^1$H NMR (CDdC$_3$) δ 3.03 (m, CH$_2$S), 4.40 (m, CH$_2$O), 4.70 (brs, 0.66H), 4.83 (brs, 0.33H), 5.45 (m, 0.33H), 5.62 (t, 0.66H, J=5 Hz), 5.73 (brs, 0.33H), 5.88 (brs, 0.,66H), 7.94 (d, 0.66H, J=7.3 Hz), 7.98 (d, 1.33H, J=7.3 Hz), 7.49 (t, 1H, J=7 Hz), 7.99 (d, 2H, J=7.3 Hz) $^{13}$C NMR (CDCl$_3$) trans isomer δ 37.9, 65.9, 80.6, 99.6, 129.5, 129.3, 128.2, 133.0, 166.2; cis isomer δ 38.5, 65.9, 82.1, 100.4, 128.3, 129.3, 133.0, 166.3.

Example 2

CIS AND TRANS 2-BENZOYLOXYMETHYL-5-ACETOXY-1,3-OXATHIOLANE

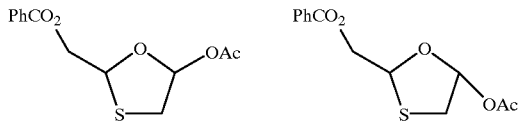

To a solution of 29.76 g (0.132 mol) of cis and trans 2-benzoyloxymethyl-5-hydroxy-1,3-oxathiolane (as prepared in Example 1) in dichloromethane (65 mL) and pyridine (32 mL) was added dropwise 28.1 mL (0.395 mol) of acetyl chloride at 0–5° C. over 1.5 to 2 hours. The reaction mixture was stirred at 0–5° C. for 30 minutes then it was poured carefully onto a cold (0° C.) solution of saturated sodium bicarbonate. The organic layer was separated and the water layer was extracted with dichloromethane (3×20 mL). The combined organic layers were washed with saturated sodium bicarbonate (3×20 mL) and brine (20 mL), and was dried over sodium sulfate. Following filtration, the solvents were removed in vacuo to give 32.1 g of crude product which was purified by Kugelrohr distillation or filtration through a short silica gel column (eluent hexanes: EtOAc 3:1). The purified product consisted of a 3:1 mixture of trans:cis isomers.

$^1$H NMR (CDCl$_3$) δ 2.09 (s, 0.75H), 2.10 (s, 2.25H), 3.22 (m, 2H), 4.54 (m, 2H), 5.68 (m, 1H), 6.64 (d, 0.25H, J=4.2 Hz), 6.72 (d, 0.75H, J=4.1 Hz), 7.45 (dd, 2H, J=7.6 Hz), 7.55 (t, 1H, J=7.3 Hz), 8.05 (dd, 2H, J=7.4 Hz). $^{13}$C NMR (CDCl$_3$) trans isomer δ 20.7, 37.3, 65.8, 83.1, 98.9, 128.2, 129.4, 129.5, 133.0, 165.7, 169.6. Cis isomer δ 20.7, 37.9, 67.5, 84.4, 99.1, 128.2, 129.4, 129.5, 133.0, 165.7, 169.5.

The trans compound can be isolated by washing the mixture with ethanol and removing the solvent in vacuo.

m.p. 67–68° C.; $^1$H NMR (DMSO-d$_6$) δ 2.10 (s, 3H), 3.18 (d, 1H), 3.39 (dd, 1H), 4.48 (d, 2H), 5.67 (d, 1H), 6.65 (d, 1H), 7.56 (m, 2H), 7.70 (m, 1H), 7.98 (m, 2H).

Example 3

TRANS-2-BENZOYLOXYMETHYL-5-ACETOXY-1,3-OXATHIOLANE

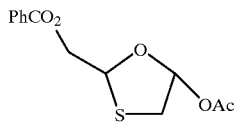

A solution benzoyloxyacetaldehyde (ca. 465 g) in toluene (ca. 2 l) was treated with 1,4-dithiane-2,5-diol (227.2 g, 1.49 mol) and the suspension was stirred and heated at 75–80° C. for 5 hours. The mixture was cooled to 25–30° C. and the remaining solid (unreacted dithiane) was collected by filtration.

The filtrate was diluted with pyridine (362 mL, 4.48 mol) and the resulting solution was cooled to 0–5° C. Acetyl chloride (316.8 mL, 4.46 mol) was added during 20 minutes such that the temperature was maintained in the range 0–20° and the mixture was then stirred at 27–30° C. for 30 minutes. The reaction mixture was cooled to 5–10° C. and 1M hydrochloric acid (1.91, 1.9 mol) was added such that the temperature was maintained in the range 5–20° C. The phases were separated and the aqueous phase was extracted with toluene (1.9 l). The combined organic phases were washed with saturated aqueous sodium bicarbonate solution (2.8 l). The organic was concentrated in vacuo at ca. 45° C. to an oil. This oil was diluted with ethanol (IMS, 3 l) and was reconcentrated to an oil. This was treated with ethanol (IMS, 2.5 l), the mixture stirred at 0–5° C. for 3.5 hours and the resultant suspension was stored at 2° C. for 17 hours. The product was isolated by filtration to give the title compound as a cream coloured solid, 147.3 g; m.p. 67–68°C.;

$^1$H NMR (DMSO-d$_6$): δ 7.98 (m, 2H, aromatic), 7.70 (m, 1H, aromatic), 7.56 (m, 2H, aromatic), 6.65 (d, 1H, C$_5$—H), 5.67 (d, 1H, C$_2$—H), 4.48 (d, 2H, CH$_2$—C$_2$), 3.39 (dd, 1H, C$_4$—H$_2$), 3.18 (d, 1H, C$_4$—H$_2$), 2.10 (s, 3H, OCO—CH$_3$).

Example 4

CIS AND TRANS 2-BENZOYLOXYMETHYL-5-(3',4'-DICHLOROBENZOYLOXY)-1,3-OXATHIOLANE

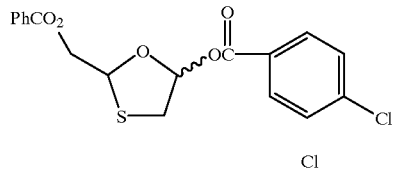

A mixture of cis and trans 2-benzoyloxymethyl-5-hydroxy-1,3-oxathiolane (as prepared in example 1) (8.99 g, 39.8 mmol) was reacted with 8.3 g (39.6 mmol) of 3,4-dichlorobenzoylchloride in-dichloromethane (30 mL) and pyridine (9.6 mL) as described in Example 2 to yield 4.86 g of the desired compounds in 1:1 ratio.

$^1$H NMR (CDCl$_3$) δ 3.35 (m, 2H), 4.55 (m, 2H), 5.72 (m, 1H), 6.80 (m, 0.5H), 6.93 (m, 0.5H), 7.26 (d, 1H, J=6.8 Hz), 7.38 (m, 1H), 7.82 (m, 2H); $^{13}$C NMR (CDCl$_3$) δ, 37.4, 38.1, 65,9, 67.3, 83.5, 84.9, 100.1, 100.4, 128.5, 129.5, 129.6, 129.7, 129.8, 130.7, 131.7, 133.1, 133.3, 133.4, 138.3, 163.5, 163.6 166.0, 166.2.

Example 5

CIS AND TRANS 2-BENZOYLOXYMETHYL-5-TRIMETHYLACETOXY-1,3-OXATHIOLANE

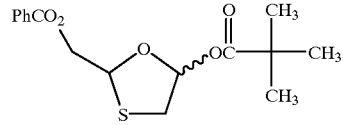

A mixture of cis and trans 2-benzoyloxymethyl-5-hydroxy-1,3-oxathiolane (8.9 g, 39.6 mmol) (as prepared in example 1) was reacted with 14.6 mL (118.8 mmol) of trimethylacetylchloride in dichloromethane (35 mL) and pyridine (9.6 mL) as described in example 2 to yield 7.94 g of the desired compound in 1:1 ratio.

$^1$H NMR (CDCl$_3$) δ 1.20 (s, 9H), 3.16 (dd, 1H), 3.30 (m, 1H), 4.50 (m, 2H), 5.60 (m, 1H), 6.65 (d, 0.5H, J=4.7 Hz), 6.68 (d, 0.5H, J=4.1 Hz), 7.43 (m, 2H), 7.53, (m, 1H), 8.05 (d, 2H, J=7.8 Hz). $^{13}$C NMR (CDCl$_3$) δ, 26.6, 37.3, 37.9, 38.4, 38.7, 66.0, 68.1, 83.1, 84.5, 99.2, 99.7, 128.5, 129.7, 129.8, 129.9, 133.3, 166.2, 177.4.

Example 6

CIS AND TRANS 2-BENZOYLOXYMETHYL-5-(2',2',2'-TRICHLOROETHOXYCARBONYLOXY)-1,3-OXATHIOLANE

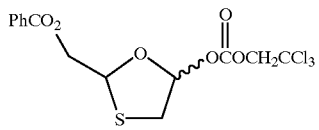

A mixture of cis and trans 2-benzoyloxymethyl-5-hydroxy-1,3-oxathiolane 4.47 g (19.8 mmol) (as prepared in example 1) was reacted with 8.2 mL (59.4 mmol) of 2,2,2-trichloroethylchloroformate in pyridine (4.8 mL) and dichloromethane (150 mL) as described in example 2 to give 6.0 g of the title compound in 2:1 ratio.

$^1$H NMR (CDCl$_3$) δ 3.32 (m, 2H), 4.74 (m, 2H), 4.80 (s, 2H), 5.71 (m, 1H), 6.55 (brs, 0.33H), 6.62 (d, 0.66H), 7.41 (dd, 2H), 7.53 (t, 1H), 8.00 (d, 2H). $^{13}$C NMR (CDCl$_3$) trans isomer δ0 37.0, 65.6, 77.0, 83.6, 93.8, 102.9, 128.4, 129.6, 129.7, 133.3, 133.4, 153.1, 165.8. Cis isomer δ 37.6, 67.6, 85.0, 93.9, 102.9, 128.4, 10 129.6, 129.7, 133.3, 152.6, 165.8.

Example 7

CIS AND TRANS-2-BENZOYLOXYMETHYL-5-ETHOXYCARBONYLOXY3-OXATHIOLANE

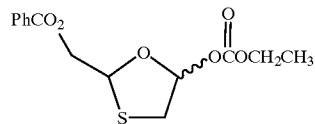

A mixture of cis and trans 2-benzoyloxymethyl-5-hydroxy-1,3-oxathiolane 1.49 g (6.6 mmol) (as prepared in Example 1) was reacted with ethylchloroformate 1.3 mL (13.2 mmol) and pyridine (3.3 mL) as described in example 2 to give 1.51 g of the title compound.

$^1$H NMR (CDCl$_3$) δ 1.19 (t, 3H, J=6.5 Hz), 3.16 (m, 2H), 4.10 (q, 2H, J=6.5), 4.43 (m, 2H), 5.61 (m, 1H), 6.45 (d, 0.33H, J=3.5 Hz), 6.54 (d, 0.66H, J=4.1 Hz), 7.36 (dd, 2H, J=7.4 Hz), 7.46 (t, 1H, 7.6 Hz), 7.95 (d, 2H, J=7.2 Hz). $^{13}$C NMR (CDCl$_3$) trans δ 13.4, 36.7, 63.7, 65.5, 82.9, 101.6, 129.3, 129.4, 128.1, 132.8, 153.4, 165.6 cis δ 13.4, 37.3, 63.7, 67.0, 84.3, 101.7, 129.3, 129.4, 128.1, 132.8, 153.3, 165.6.

Example 8

CIS AND TRANS-2-CARBOETHOXY-5-HYDROXY-1,3-OXATHIOLANE

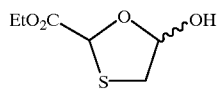

A mixture of the mercaptoacetaldehyde dimer (5.1 g, 33.65 mmol), ethyl glyoxylate (8.58 g, 2.5 equivalents), and a magnetic stirring bar were placed in a round bottom flask. After flushing with argon, the mixture was heated with a heat gun with stirring until a pale yellow oil was obtained (about 3 to 5 minutes). The crude product was then purified by flash column chromatography (45% ethyl acetate in hexanes) to give the desired material (7 g, 58% yield) as a mixture of isomers epimeric at C-5.

Note: Ethyl glyoxylate was prepared according to the procedure reported by T. R. Kelly and coworkers [Synthesis, 544 (1972)].

$^1$H NMR (CDCl$_3$) δ 1.30 (m, 3H), 3.11 (m, 2H), 4.21 (m, 2H), 5.56 (s, 0.5H), 5.59 (s, 0.5H), 5.89 (m, 0.5H), 6.02 (m, 0.5H) $^{13}$C NMR (CDCl$_3$) δ 13.7, 38.2, 40.0. 61.8, 62.5, 77.7, 79.8, 101.3, 103.0, 170.1.

Example 9

CIS AND TRANS 2-CARBOETHOXY-5-METHOXYCARBONYLOXY-1,3-OXATHIOLANE

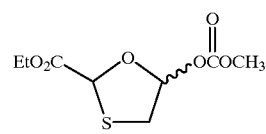

To a cold (−25° C.) stirred solution of the crude hydroxy compound (10 g) (as prepared in example 8) and pyridine (9.1 mL, 0.113 mmol) in dry dichloromethane (20 mL) under argon was added methyl chloroformate (8.7 mL, 0.113 mmol) slowly over a period of 5 minutes. Upon completion of addition, the cooling bath was removed and the reaction mixture was stirred for 3 hours. Water (20 mL) was added to the mixture and stirring was continued for another 5 minutes. The resulting mixture was diluted with dichloromethane (150 mL) and washed with 1 M HCl (3×40 mL), saturated sodium bicarbonate (40 mL), brine (40 mL), and then was dried over sodium sulphate. Removal of the solvent under reduced pressure gave 9.2 g of the crude product which was purified by flash column chromatography (25% ethyl acetate in hexanes). The trans carbonate was obtained in pure form (4.02 g), as indicated by the NMR spectrum of the material. However, an additional 1.65 g was obtained and found to be contaminated with the trans compound (20%) as determined by NMR integration.

$^1$H NMR (CDCl$_3$) trans δ 1.29 (t, 3H, J=7.1 Hz), 3.24 (d, 1H, J=11.9 Hz), 3.44 (d of d, 1H, J=4.1, 11.9 Hz), 3.82 (s, 3H), 4.24 (q, 2H, J=7.1 Hz), 5.65 (s, 1H), 6.69 (d, 1H, J=4.1 Hz).

Example 10

CIS AND TRANS 2-CARBOETHOXY-5-ACETOXY-1,3-OXATHIOLANE

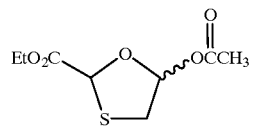

To a cold (0° C.) stirred solution of the hydroxy compound (6.0 g, 33.7 mmol) obtained as in Example 8, and pyridine (5.45 mL) in dry dichloromethane (25 mL) under argon was added slowly acetyl chloride (3.60 mL, 1.5 equivalents) over a period of 20 minutes. The resultant mixture was stirred for 1 hour and 45 minutes. Analysis of the reaction mixture by TLC showed that all starting material was consumed. The excess acetyl chloride was quenched by the addition of methanol (2 mL). The mixture was diluted with ether (150 mL) and was washed with water (3×40 mL), 1 M HCL (40 mL) saturated sodium bicarbonate (40 mL), and then dried over anhydrous sodium sulphate. Removal of the solvent under reduced pressure gave 4.67 g of the crude product. The combined aqueous washings was extracted with ethyl acetate (3×50 mL). Concentration of the extract provided another 1 g of the crude product. The combined crude product was subjected to flash column chromatography (25% ethyl acetate in hexanes) to afford 2.2 g of the trans acetate (the less polar component). The corresponding cis acetate was obtained as a mixture (1.71 g) contaminated with small amount of the trans isomer.

$^1$H NMR (CDCl$_3$) trans δ 1.30 (t, 3H, J=7.1 Hz), 2.10 (s, 3H), 3.17 (d, 1H, J=11.8 Hz), 3.44 (dd, 1H, J=9, 11.8 Hz), 4.25 (q, 2H, J=7.1 Hz), 5.65 (s, 1H), 6.80 (d, 1H, J=4.0 Hz).

Example 11

TRANS-2-HYDROXYMETHYL-5-ACETOXY-1, 3-OXATHIOLANE

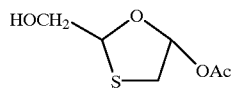

Sodium borohydride (27 mg, 0.708 mmol) was added to a magnetically stirred solution of trans-2-carboethoxy-5-acetoxy-1,3-oxathiolane (52 mg, 0.236 mmol) in methanol (1 mL) at 0° C. under an argon atmosphere. The resultant solution was stirred for 25 minutes at 0° C. The reaction was quenched with 2 drops of saturated ammonium chloride solution followed by dilution with diethyl ether (4 mL). This mixture was stirred at room temperature for 15 minutes and then was dried over anhydrous magnesium sulphate. The drying agent was removed by suction filtration and the filtrate was concentrated under reduced pressure. The crude product obtained was subjected to column chromatography (50% EtOAc-hexane) to afford 21 mg (50%) of the title compound.

$^1$H NMR (CDCl$_3$) δ: 2.11 (s, 3H), 2.22–2.35 (m,1H), 3.16 (d, 1H, J=11.6 Hz), 3.33 (d of d, 1H, J=4.2, 11.6 Hz), 3.70–3.92 (m,2H), 5.46–5.54 (m,1H), 6.69 (d, 1H, J=4.2 Hz).

Example 12

CIS AND TRANIS-2-BENZOYLOXYMETHYL-5-METHOXYCARBONYLOXY-1,3-OXATHIOLANE

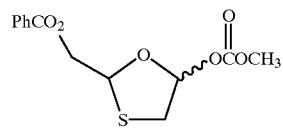

A solution of 17.93 g (0.118 mmol) of mercaptoacetaldehyde dimer and 38.70 g (0.236 mmol) of benzoyloxyacetaldehyde in 57.3 mL (3 eq) of pyridine was heated until all the solid dissolved. After cooling, 300 mL of anhydrous methylene chloride were added and the mixture was cooled at 0° C. for ca. 30 minutes. To this solution at 0° C., was slowly added a solution of methylchloroformate (57.3 mL, 0.71 mmol) in 80 mL of methylene chloride. The mixture was stirred for 12 hrs and diluted with ca. 200 mL of methylene chloride and washed several times with brine to remove pyridinium salt and then the organic layer was washed with water. The organic layer was dried over magnesium sulphate at 0° C. and then filtered. Residual pyridine was removed in vacuo and the organic residue was purified by flash chromatography using hexanes:ethyl acetate (2:1) as eluent to yield a mixture of 2:1 trans:cis carbonates (56.3 g, 80%).

$^1$H NMR (CDCl$_3$) δ 3.25 (d, 1H, J=3.1 Hz), 3.30 (dd, 1H, J=3:1 Hz), 3.73 (s, 0.1 H), 3.75 (s, 2 H), 4.47 (m, 2H), 5.66 (m, 2H), 6.50 (brd, 0.33H), 6.56 (d, 0.66H, J=3.81 Hz), 7.38 (d, 2H, J=7.3 Hz), 7.51 (t,1H, J=7.2 Hz), 8.00 (dd, 2H, J=7.3 Hz). $^{13}$C NMR (CDCl$_3$) trans isomer δ 36.9, 54.6, 65.7, 83.2, 101.9, 126.3, 128.4, 128.5, 133.1, 154.3, 166.0, cis isomer δ 37.6, 54.6, 67.3, 84.7, 102.1, 126.3, 128.4, 128.5, 133.1, 154.3, 165.9.

Example 13

CIS-2-CARBOETHOXY-5-(URACIL-1'-YL)-1,3-OXATHIOLANE

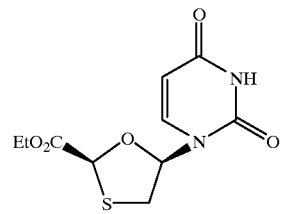

To a stirred solution of the acetate (468 mg, 2.13 mmol) as obtained in example 10 and bis-silylated uracil (653 mg, 1.2 equivalents) in dichloromethane under argon was added trimethylsilyl iodide (303 μL, 1 equivalent). The resultant yellow solution was stirred for 6.5 hours at room temperature. As indicated by TLC (silica gel), all starting material was consumed. The reaction was quenched with a 1:1 mixture of saturated solutions of sodium bicarbonate and sodium thiosulphate (5 mL). After 15 minutes of stirring, the mixture was transferred to a separatory-funnel with the aid of more dichloromethane (30 mL). The aqueous phase was removed and the organic layer was washed with saturated sodium bicarbonate-sodium thiosulphate solution 1:1, 10 ml, water (10 mL), brine (10 mL), and then was dried over anhydrous sodium sulphate. Removal of the solvent under reduced pressure gave the crude product which was triturated with a 1:1 mixture of ethyl acetate-hexane (about 10 mL). The precipitate was collected by suction filtration and then was dried under vacuum to afford 346 mg (60%) of the nucleoside as a crystalline white solid. Analysis of the triturate by TLC showed that it contained the desired product but no attempt was made to isolate these compound. The 300 MHz proton NMR spectrum of the product indicated that it consisted of one isomer only.

$^1$H NMR (CDCl$_3$) δ 1.34 (t, 3H, J=7.2 Hz), 3.16 (dd, 1H, J=7.7 Hz), 3.42 (dd, 1H, J=4.8, 12.0 Hz), 4.29 (q, 2H, J=7.1 Hz), 5.82 (dd, 1H, J=2.1, 8.2 Hz), 6.46 (dd, 1H, J=4.7, 7.5 Hz), 8.32 (d, 1H, J=8.2 Hz), 8.53 (brs, 1H) $^{13}$C NMR (CDCl$_3$) δ 14.2, 35.4, 62.8, 78.1, 89.5, 103.5, 140.8, 151.1, 163.9, 170.9

Example 14

CIS-2-CARBOETHOXY-5-(URACIL-1'-YL)-1,3-OXATHIOLANE

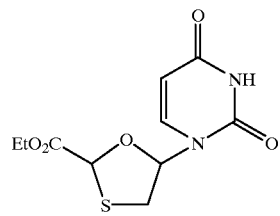

To a stirred solution of a mixture of the cis and trans carbonates (Example 9) (4:1 by NMR) (60 mg, 0.254 mmol) and silylated uracil (78 mg, 1.2 equivalents) in dry dichloromethane (1.5 mL) under argon was added TMS-I (36 μL, 1.0 equivalent). The resultant light yellow suspension was stirred at room temperature for 80 minutes at which time all starting material was consumed (TLC). The reaction was quenched with a 1:1 mixture (1 mL) of saturated sodium bicarbonate and sodium thiosulphate followed by dilution with dichloromethane (4 mL). The mixture was stirred until a colorless biphasic suspension was obtained. This suspension was transferred to a separatory funnel with the aid of more dichloromethane (25 mL) and was washed with saturated sodium thiosulphate, brine, and then was dried over anhydrous sodium sulphate. Removal of the solvent in vacuo provided the crude product. Trituration of the crude product with a 1:1 mixture (3 mL) of dichloromethane and ethyl acetate gave a white solid which was collected by suction filtration and was dried under vacuum (31 mg). The NMR spectrum of this material indicated that it consisted of the cis nucleoside only. The triturate was concentrated under reduced pressure and then was subjected to flash column chromatography (1:1 ethyl acetate-dichloromethane) to produce another 8 mg of white solid. The NMR spectrum of this substance showed that it was a 2.5:1 mixture of the cis and trans nucleosides favouring the cis isomer. The total yield of this reaction was 58% and the stereoselectivity was about 13:1 in favour of the cis isomer which displayed the same physical data as reported in Example 13.

Example 15

CIS-2-HYDROXYMETHYL-5-(URACIL-1'-YL)-1,3-OXATHIOLANE

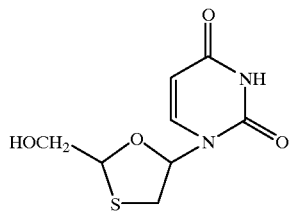

To a stirred solution of the condensation product obtained in examples 13 or 14, (33 mg, 0.107 mmol) in a solvent mixture (2:1) of dichloromethane-methanol (1.5 mL) at room temperature under argon was introduced sodium borohydride (8 mg, 2 equivalents). The resulting mixture was stirred for 1 hour. Analysis of the reaction mixture by TLC indicated that substantial amount of starting material was present. More hydride (approx. 10 mg) was added and stirring was continued for another 1.5 hours. The excess hydride was quenched by addition of one drop of saturated ammonium chloride solution. After dilution with tetrahydrofuran (3 mL), the gelatinous mixture was stirred for 30 minutes. The inorganic salt was removed by suction filtration through a pad of celite. Concentration of the filtrate under reduced pressure provided the crude product which was subjected to column chromatography (100% ethyl acetate, silica gel) to afford the desired alcohol (25 mg, 90%) as a white solid.

The 300 MHz proton NMR spectrum of the compound thus obtained was found to be identical to that prepared according to different procedures. Thus, the stereochemistry of the nucleoside generated by this new route was established.

$^1$H NMR (DMSO) δ 3.23 (d of d, 1H, J=4.4, 12.0 Hz), 3.45 (d of d, 1H, J=5.6, 11.9 Hz), 3.75 (d, 2H, J=4.4 Hz), 5.20 (t, 1H, J=4.4 Hz), 5.36 (brs, 1H), 5.65 (d of d, 1H, J=2.1, 8.2 Hz), 6.21 (t, 1H, J=5.1 Hz), 7.92 (d, 1H, J=8.2 Hz). $^{13}$C NMR (DMSO)=δ 36.02, 62.54, 85.91, 86.48, 101.82, 141.05, 150.63, 163.71.

Example 16

CIS-2-CARBOETHOXY-5-(N-ACETYLCYTOSIN-1'-YL)-1,3-OXATHIOLANE

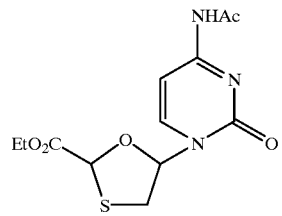

To a stirred suspension of N-acetylcytosine (237 mg, 1.40 mmol) in dichloromethane (2.5 mL) containing 2,6-lutidine (326 μL, 1.40 mmol) was added slowly trimethylsilyl trifluoromethanesulphonate (540 μL, 3.07 mmol). The resultant mixture was stirred for 15 minutes to give a homogeneous solution. A mixture of cis and trans-2-carboethoxy-5-methoxycarbonyloxy-1,3-oxathiolane (example 9) (300 mg, 1.27 mmol), dissolved in dichloromethane (2 mL),-was introduced to the above solution followed by the addition of iodotrimethylsilane (181 μL, 1.27 mmol). The reaction mixture was kept at room temperature for 1 hour and 40 minutes. Water (2 mL), saturated sodium thiosulphate (4 mL) and dichloromethane (6 mL) were added to quench the reaction. The resulting mixture was stirred vigorously for 10 minutes and then was transferred to a separatory funnel with the aid of more dichloromethane (30 mL). The aqueous phase was removed and the organic phase was washed successively with saturated sodium thiosulphate (10 mL), water (10 mL), 1 M hydrochloric acid (10 mL), saturated sodium bicarbonate (10 mL), brine (10 mL), and then was dried (sodium sulphate). The solvent was evaporated under reduced pressure to give the crude product as a light yellow solid (395 mg). The $^1$H NMR spectrum of this material indicated that a 7.5:1 (in favour of the cis isomer) mixture of the expected coupling products was obtained. This material was triturated with a mixture of dichloromethane (1.5 mL) and a solution of ethyl acetate-hexane (1:1) (6 mL). The white solid formed was collected by suction filtration and was dried under vacuum to afford 262 mg (63% yield) of the desired product as a white powder. The $^1$H NMR spectrum of the substance indicated an isomeric purity of greater than 95%. The triturate was concentrated and then was subjected to flash column chromatography (5% MeOH-EtOAc) to provide another 58 mg (14% yield) of the nucleosides as a 1:1 mixture of the cis and trans isomers ($^1$H NMR). The title compound displayed the following spectral characteristics:

$^1$H NMR (CDCl$_3$) δ 1.34 (t, 3H, J=7.1 Hz), 2.28 (s, 3H), 3.23 (d of d, 1H, J=12.3, 5.6 Hz), 3.68 (d of d, 1H, J=12.4, 4.8 Hz), 4.31 (q, 2H, J=7.1 Hz), 5.56 (s, 1H), 6.43 (t, 1H, J=5.2 Hz), 7.47 (d, 1H, J=7.5 Hz), 8.76 (br. d, 1H, J=7.4 Hz), 8.30–9.00 (unresolved m, 1H).

Example 17

CIS-2-CARBOETHOXY-5-(CYTOSIN-1'-YL)-1,3-OXATHIOLANE

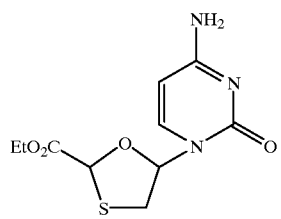

A mixture of cis-2-carboethoxy-5-(N4'-acetylcytosin-1'-yl)-1,3-oxathiolane (example 16) (20 mg, 0.061 mmol) in ethanol (1 mL) containing trifluoroacetic acid (9.4 μL, 0.25 mmol) was refluxed under argon for 3 hours and 10 minutes. On cooling to room temperature, a crystalline white solid was formed. This solid was collected by suction filtration and was dried under vacuum to afford 15 mg (86%) of the desired product. The title compound displayed the following spectral characteristics: $^1$H NMR (DMSO) δ 1.23 (t, 3H, J=7.1 Hz), 3.32 (d of d, 1H, J=12.4, 5.2 Hz), 3.63 (d of d, 1H, J=12.3, 5.2 Hz), 4.21 (q, 2H, J=7.1 Hz), 5.80 (s, 1H), 6.08 (d, 1H, J=7.7 Hz), 6.32 (t, 1H, J=5.1 Hz), 8.19 (d, 1H, J=7.7 Hz), 8.35 (brs, 1H), 9.12 (brs, 1H).

Example 18

CIS-2-HYDROXYMETHYL-5-(CYTOSIN-1'-YL)-1,3-OXATHIOLANE (BCH-189)

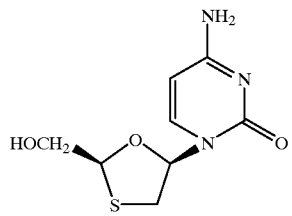

To a stirred suspension of cis-2-carboethoxy-5-(cytosin-1'-yl)-1,3-oxathiolane (Example 17) (36 mg, 0.125 mmol) is ethanol at 0° C. under argon was added sodium borohydride (9.5 mg, 0.250 mmol). The resultant mixture was stirred for 2 hours 30 minutes at (0° C. to RT). The reaction was quenched by the addition of one drop of concentrated ammonium hydroxide, followed by dilution with methanol (1 mL). After the mixture had been stirred for 15 minutes, the solvent was removed under reduced pressure. The crude product thus obtained was subjected to column chromatography (25% MeOH-EtOAc) to afford 26 mg (85%) of the desired product. The title compound displayed spectral characteristics identical to that reported for BCH-189.

Example 19

CIS AND TRANS 2-BENZOYLOXYMETHYL-5-(CYTOSIN-1'-YL)-1,3-OXATHIOLANE

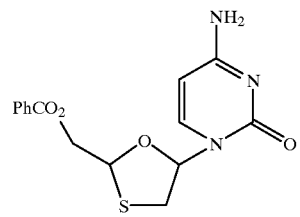

To a solution maintained at 0° C. of 2.14 g (7.2 mmol) of carbonate (as in example 7) in 10 mL of freshly distilled 1,2-dichloroethane was added 0.37 g (0.36 mmol) of fused ZnCl$_2$ and 2.7 mL (2.7 mmol) of TiCl$_4$. After stirring for 5 minutes a solution of silylated cytosine (from 1 g of cytosine silylated with 1,1,1,3,3,3,-hexamethyldisilazane) in 25 mL of freshly distilled 1,2-dichloroethane was added via a canula (10–15 min.) The reaction was allowed to warm to RT (3 hours) and stirring continued for 11 hours followed by a short reflux (20 min). The solution was then cooled and quenched with saturated sodium bicarbonate (30 mL). After stirring for 15 min. the two phase solution was separated and the organic layer together with the emulsion was filtered through a celite. The aqueous layer was extracted (3×20 mL) with CH$_2$Cl$_2$ and the combined organic layers were washed with brine, separated and dried over MgSO$_4$. The oil obtained from the organic layer, by evaporation of the solvents in vacuo, was purified by chromatography on silica gel using gradient elution (1:1 hexanes:EtOAc-9:1 EtOAc:MeOH) to yield 1.32 g of trans and cis isomers (trans/cis =3.5/5 as determined by $^1$H NMR). Spectral properties were identical to those reported earlier.

By varying the amount and the nature of the Lewis acid the yield and the ratio of the trans to cis isomers were as follows:

| Lewis Acid | Yield | trans/cis ratio |
| --- | --- | --- |
| 0.25 eq. TiCl$_4$ | 31% | 1/1.2 |
| 0.40 eq. TiCl$_4$ | 50% | 1/1.3 |
| 0.3 eq. TiCl$_4$ | 60% | 1/1.6 |
| 0.2 eq. ZnCl$_2$ | | |

Example 20

CIS AND TRANS 2-BENZOYLOXYMETHYL-5-(N4'-ACETYL CYTOSIN-1'-YL)-1,3-OXATHIOLANE

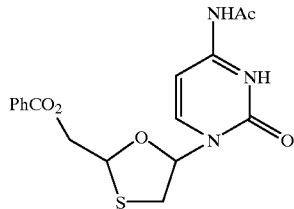

To a solution maintained at 0° C. of 2.14 g (7.2 mmol) of trans 2-benzoyloxymethyl-5-acetoxy-1,3-oxathiolane (as in Example 3) in 10 mL of freshly distilled acetonitrile was added a solution of silylated cytosine N-acetylcytosine (from 1.37 g of N-acetylcytosine silylated with 1,1,1,3,3,3,-hexamethyldisilazane) in 25 mL of freshly distilled 1,2-dichloroethane via a canula (10–15 min.) and 0.2 mL of iodotrimethylsilane. The reaction was allowed to stir at 0° C. (3 hours) and stirring continued for 11 hours at RT. The solution was then cooled and quenched with saturated sodium bicarbonate (30 mL). After stirring for 15 min. the two phase solution was separated and the organic layer together with the emulsion was filtered through a celite. The aqueous layer was extracted (3×20 mL) with $CH_2Cl_2$ and the combined organic layers were washed with brine, separated and dried over $MgSO_4$. The oil obtained from the organic layer, by evaporation of the solvents in vacuo, was purified by chromatography on silica gel using gradient e-lution (1:1 hexanes:EtOAc-9:1 EtOAc: MeOH) to yield 2.43 g of trans and cis isomers (trans/cis=3/7 as determined by $^1H$ NMR). The physical properties are identical to those reported earlier.

Replacement of iodotrimethylsilane by trimethylsilyltriflate in dichloromethane at RT yielded 2.43 g of trans and cis isomers in 1:1 ratio as determined by $^1H$ NMR.

Example 21

CIS-2-HYDROXYMETHYL-5-(CYTOSIN-1-YL)-1,3-OXATHIOLANE

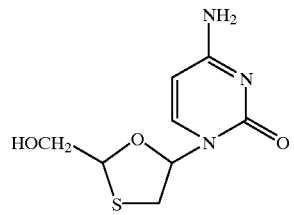

A suspension of cis-2-benzoyloxymethyl-5-(cytosin-1'-yl)-1,3-oxathiolane (200 g, 0.54 mol) and Amberlite IRA 400 (OH) ion-exchange resin (600 g) in IMS was stirred and heated to 60–65° C. The suspension was maintained at this temperature range for 1 hour, and filtered hot. The resin was washed with IMS at 60° C. (200 mL). The combined filtrates were filtered twice through celite J2 and the celite washed sequentially with IMS at 60° C. (200 mL) and water at 50–60° C. (100 mL). The combined filtrates were distilled under atmospheric pressure to a volume of 500 mL. Absolute ethanol was added, and the distillation continued until a further 700 mL had been removed. The resultant suspension was allowed to cool, and then stirred overnight at 0–5° C. The suspension was filtered, the product washed with IMS at 0° C. (2×25 mL), and dried overnight in vacuo at 45–50° C. to give the title compound, 81.9 g.

Example 22

CIS- AND TRANS-2-ACETOXYMETHYL-5-ACETOXY-1,3-OXATHIOLANE

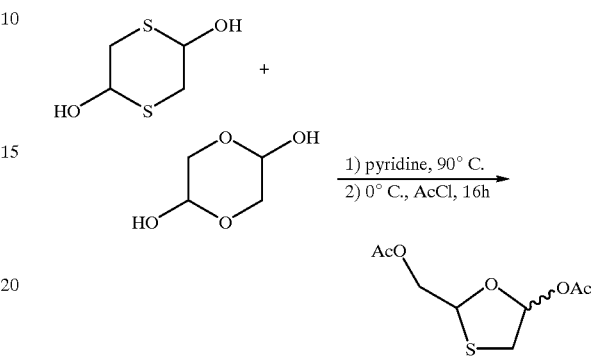

A mixture of glycoaldehyde (1.2 g, 0.01 mol) and mercaptoacetaldehyde dimer (1.52 g, 0.01 mol) in dry pyridine (20 ml) was heated at 90° C. for 2 h. The clear solution was then cooled in an ice-bath to 0° C., followed by adding acetyl chloride (2.8 ml). The mixture was stirred at room temperature overnight (16 h), and poured into saturated aqueous $NaHCO_3$ solution (100 ml). The product was extracted into methylene chloride (3×100 ml), washed with water (2×100 ml), dried over $MgSO_4$ and filtered. The solvent was removed on an evaporator and the oily residue was purified on silica gel hexane:EtOAc 9:1 as eluant to give the product (2.8 g) in 59% yield as a mixture of 1:1 cis:trans isomers.

$^1H$-NMR (300 MHz, $CDCl_3$): δ in ppm; 6.68 (d, 1H, H-5, trans-isomer, J=4.1 Hz); 6.61 (d, 1H, H-5, cis-isomer, J=4.4 Hz); 5.52 (m, 2H, H-2, cis and trans-isomers); 4.37 (dd, 1H, —$CH_2OAc$, cis-isomer, J=8.0 and 11.7 Hz); 4.26 (m, 2H, —$CH_2OAc$, trans-isomer); 4.13 (dd, 1H, —$CH_2OAc$, cis-isomer, J=4.1 and 11.8 Hz); 3.33 (dd, 2H, H-4, cis and trans isomers); 3.11 (dd, 2H, H-4, cis and trans-isomers); 2.11 (s, 3H, $CH_3$—); 2.08 (s, 3H, $CH_3$—);

Example 23

CIS- AND TRANS-2-BENZOYLOXYMETHYL-5-BENZOYL-1,3-OXATHIOLANE

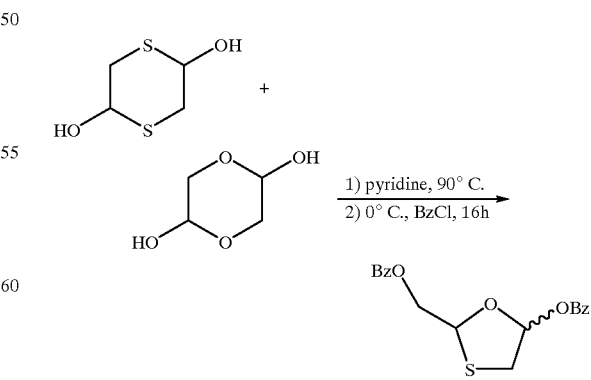

A mixture of glycoaldehyde (1.2 g, 0.01 mol) and mercaptoacetaldehyde dimer (1.52 g, 0.01 mol) in dry pyridine (20 ml) was heated at 90° C. for 2 h. The clear solution was then cooled in an ice-bath to 0° C., followed by adding benzoyl chloride (4.6 ml). The mixture was stirred at room temperature overnight (16 h), and poured into saturated aqueous NaHCO₃ solution (100 ml). The product was extracted into methylene chloride (3×100 ml), washed with water (2×100 ml), dried over MgSO₄ and filtered. The solvent was removed on an evaporator and the oily residue was purified on silica gel using hexane:EtOAc 9:1 as eluant to give the product (3.65 g) in 53% yield as a mixture of 1:1 cis and trans isomers.

¹H-NMR (300 MHz, CDCl₃): δ in ppm; 8.05 (m, aromatic); 7.57 (m, aromatic); 7.45 (m, 4H, aromatic); 6.98 (d, 1H, H-5, trans-isomer, J=3.9 Hz); 6.90 (d, 1H, H-2, cis-isomer, J=3.0 Hz); 5.79 (t, 1H, H-2, trans-isomer, J=5.2 Hz); 5.74 (dd, 1H, H-2, cis-isomer, J=4.9 and 7.3 Hz); 4.58 (m, 4H, —CH₂OBz, cis and trans-isomers); 3.45 (m, 2H, H-4, cis and trans isomers); 3.35 (m, 2H, H-4, cis and trans-isomers).

Example 24

CIS- AND TRANS-ETHYL 5-IODO-1,3-OXATHIOLAN-2-CARBOXYLATE

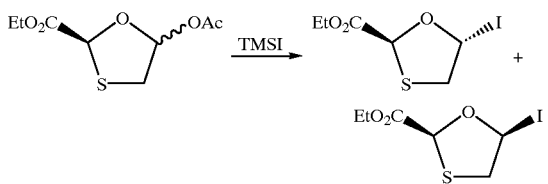

The starting material (21.5 mg, 0.0976 mmol, cis:trans=1:1) in dichloromethane-d₂ (0.6 mL) at −78° C. under argon atmosphere wa treated with iodotrimethylsilane (0.014 mL, 0.0976 mmol). The slightly yellow solution was left at room temperature for two hours. The starting acetoxyoxathiolane compounds were completely converted to the iodo intermediates and trimethylsilyl acetate. The iodo compounds (in a 6.7:1 ratio of cis to trans isomer) are unstable to the moisture and had to be used without any purification.

¹H NMR (CD₂Cl₂): δ 0.00 (s, 9H), 1.05 (t, 3H, J=7.1 Hz), 1.80 (s, 3H), 3.25–3.50 (m, 2H), 4.00 (q, 2H, J=7.1 Hz), 5.43 (s, 0.13H), 5.48 (s, 0.87H) 6.64 (ddd, 0.13H, J=4.3, 2.9, 0.7 Hz), 7.00 (dt, 0.87H, J=4.0, 0.7 Hz); ¹³C NMR (CD₂Cl₂): δ 0.3, 2.5, 14.8, 23.5, 47.7, 48.2, 63.1, 65.5, 69.7, 81.6, 83.7, 168.6.

Example 25

CIS- AND TRANS-ETHYL 5-(6' CHLOROPURIN-9'-YL)-1,3-OXATHIOLAN-2-CARBOXYLATE; and CIS- AND TRANS-ETHYL 5-(6' CHLOROPURIN-7'-YL)-1,3-OXATHIOLAN-2-CARBOXYLATE

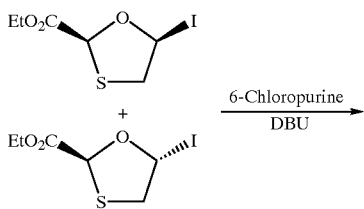

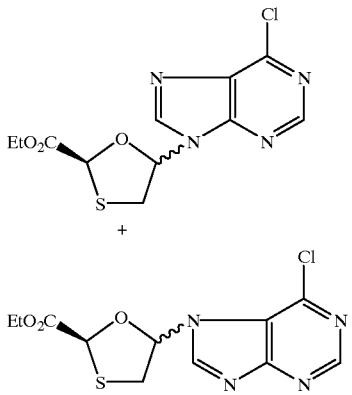

To the 6-chloropurine (15 mg, 0.0976 mmol) in dichloromethane-d₂ (0.15 mL) at room temperature under argon atmosphere was added 1,8-diazabicyclo[5,4,0] undec-7-ene (0.015 mL, 0.0976 mmol). The solution thus formed was added to the iodo intermediates prepared above in dichloromethane-d₂ at −78° C. The mixture was allowed to stay at room temperature for 4 hours and then diluted with dichloromethane (20 mL), washed with saturated aqueus sodium bicarbonate, 1N aqueous hydrogen chloride, water and brine, dried and concentrated. The residue was chromatographed on silica gel with ethyl acetate-dichloromethane to afford the N-9 linked isomers (11.6 mg, 38%, cis:trans=11:1) and N-7 linked isomers (4.4 mg, 14.3%, cis:trans=8.4:1).

¹H NMR for N-9 isomers (CDCl₃): δ 1.26 (t, 3H, J=7.1 Hz), 3.65 (m, 2H), 4.26 (q, 2H, J=7.1 Hz), 5.62 (s, 0.92H), 5.80 (s, 0.08H), 6.75 (t, 0.92H, J=5.4 Hz), 7.02 (dd, J=6.2, 2.0 Hz), 8.39 (s, 0.08H), 8.73 (s, 0.92 Hz), 8.89 (s, 0.92 Hz); ¹H NMR for the N-7 isomers (CDCl₃): δ 1.30 (t, 3H, J=7.1 Hz), 3.38 (d, 0.12H, J=12.5 Hz), 3.54 (dd, 0.88H, J=12.5, 4.5 Hz), 3.75 (dd, 0.88H, J=14.5, 4.5 Hz), 3.96 (dd, 0.12H, J=12.5, 4.5 Hz), 4.29 (q, 2H, J=7.1 Hz), 5.69 (s, 0.88H), 5.90 (s, 0.12H), 7.07 (t, 0.88H, J=4.5 Hz), 7.35 (d, 0.12H, J=4.5 Hz), 8.45 (s, 0.12H), 8.92 (s, 1H), 9.20 (s, 0.88H)

What is claimed is:

1. A process comprising:

reacting mercaptoacetaldehyde with a compound of formula R_yOOCCHO, wherein R_y is C_{1-12} alkyl or C_{6-20} aryl to obtain a compound of formula (XV)

(XV)

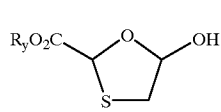

wherein said mercaptoacetaldehyde is the monomer of 1,4-dithiane-2,5 diol.

2. The process according to claim 1, wherein the mercaptoacetaldehyde monomer is obtained from 1,4-dithianc-2,5-diol dissolved in an inert solvent.

3. The process according to claim 2, wherein said inert solvent is selected from group consisting of: pyridine, toluene and DMSO.

4. A process according to claim 1, wherein said compound of formula R_yOOCCHO is ethyl gloxylate.

5. The process according to claim 1, further comprising converting the hydroxyl of the compound of formula (XV) to a leaving group L to obtain a compound of formula (XVI):

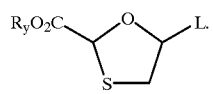

(XVI)

6. The process according to claim 5, wherein L is $OR_z$, wherein $R_z$ is selected from the group consisting of; a saturated or unsaturated $C_{1-6}$ alkyl group, an aliphatic or aromatic $C_{1-6}$ acyl group, a saturated or unsaturated alkoxycarbonyl group, a sulphonyl imidazolide, a carbonyl imidazolide, a aliphatic or aromatic amino carbonyl group, a alkyl imidate group, a saturated or unsaturated phosphinoyl, and a aliphatic or aromatic sulphonyl group.

7. The process according to claim 5 further comprising: reacting the compound of formula (XVI) with a silylated —$R_2$ compound in the presence of a Lewis acid, whereby said leaving group is displaced, to produce a compound of formula (XVII):

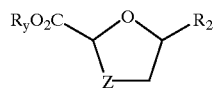

(XVII)

wherein
Z is S,
$R_2$ is selected from the group consisting of:

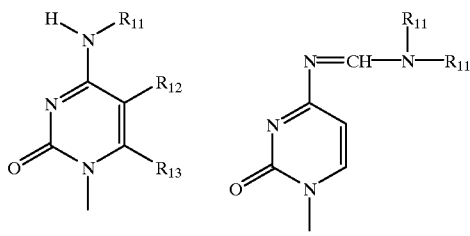

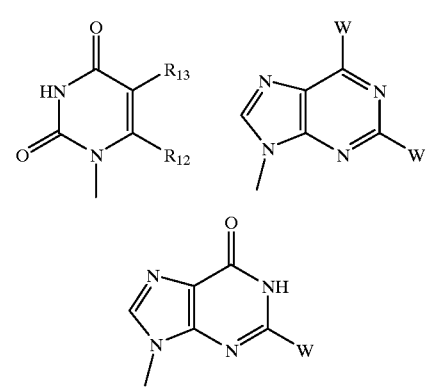

$R_{11}$ is in each case independently selected from hydrogen, acetyl, and $C_{1-6}$ alkyl;
$R_{12}$ and $R_{13}$ are each independently selected from hydrogen, hydroxymethyl, trifluoromethyl, $C_{1-6}$ alkyl or alkenyl, bromine, chlorine, fluorine, and iodine; and
W is in each case independently selected from hydrogen, bromine, chlorine, fluorine, iodine, amino, and hydroxyl.

8. The process according to claim 5 or 6, further comprising:

(a) converting the group $R_yO_2C$ of the compound of formula (XVI) to hydroxymethyl ($HOCH_2$); and (b) protecting the resulting hydroxymethyl with a protecting function $R_1$ to obtain a compound of formula (XXII):

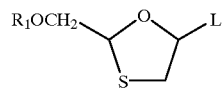

(XXII)

wherein $R_1$ is selected from the group consisting of $C_{1-16}$ acyl, t-butyldimethylsilyl, and t-butyldiphenylsily.

9. The process according to claim 8, further comprising: reacting the compound of formula (XXII) with a silylated —$R_2$ compound, in the presence of a Lewis acid, whereby said leaving group is displaced, to obtain a compound of formula (XXIII):

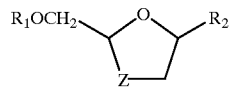

(XXIII)

wherein
$R_2$ is selected from the group consisting of

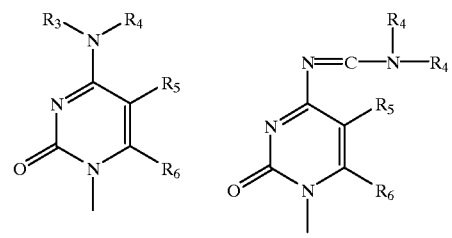

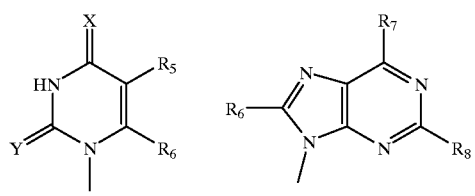

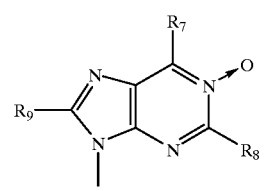

wherein:
X is oxygen or sulfur; Y is oxygen or sulfur;
$R_3$ and $R_4$ are independently selected from the group consisting of hydrogen, hydroxyl, amino, $C_{1-6}$ alkyl, alkenyl, $C_{2-6}$ alkynyl, and $C_{1-10}$ acyl or aracyl;
$R_5$ and $R_6$ are independently selected from the group consisting of hydrogen, halogen, hydroxyl, amino, cyano, carboxy, carbamoyl, alkoxycarbonyl, hydroxymethyl, trifluoromethyl, thioaryl, $C_{1-6}$ alkyl, $C_{2-6}$ alkenyl, $C_{2-6}$ alkynyl, and $C_{1-10}$ acyloxy;

$R_7$ and $R_8$ are independently selected from the group consisting of hydrogen, hydroxy, alkoxy, thiol, thioalkyl, amino, halogen, cyano, carboxy, alkoxycarbonyl, carbamoyl, $C_{1-6}$ alkyl, $C_{2-6}$ alkenyl, $C_{2-6}$ alkynyl, and $C_{1-10}$ acyloxy; and $R_9$ is selected from the group consisting of hydrogen, hydroxy, alkoxy, amino, halogen, azido, $C_{1-6}$ alkyl, $C_{2-6}$ alkenyl, $C_{2-6}$ alkynyl, and $C_{1-10}$ acylo and Z is S; and optionally further comprising oxidizing Z of said compound of formula (XXIII) to obtain a compound of formula (XXIII) wherein Z is S=O or $SO_2$.

10. The process according to claim 9, further comprising converting $R_1OCH_2$ from compound (XXIII) to hydroxymethyl ($HOCH_2$) to obtain a compound of formula (I):

(I)

11. The process according to claim 9, wherein the Lewis acid is selected from the group consisting of: TMSOTf, TMSI, $TiCl_4$ and $SnCl_4$.

12. The process according to claim 5, further comprising:

(a) reacting the compound of formula (XVI) with a halogen-containing Lewis acid to obtain a compound of formula (XXVI):

(XXVI)

wherein Hal is a halogen and (b) coupling the compound of formula (XXVI) with a purine compound, under basic condition, whereby said halogen is displaced to obtain a compound of formula (XVII):

(XVII)

wherein $R_2$ is selected from the group consisting of:

-continued wherein:

X is oxygen or sulfur;

Y is oxygen or sulfur;

$R_3$ and $R_4$ are independently selected from the group consisting of hydrogen, hydroxyl, amino, $C_{1-6}$ alkyl, $C_{2-6}$ alkenyl, $C_{2-6}$ alkynyl, and $C_{1-10}$ acyl or aracyl;

$R_5$ and $R_6$ are independently selected from the group consisting of hydrogen, halogen, hydroxyl, amino, cyano, carboxy, carbamoyl, alkoxycarbonyl. hydroxymethyl, trifluoromethyl, thioaryl, $C_{1-6}$ alkyl, $C_{2-6}$ alkenyl, $C_{2-6}$ alkynyl, and $C_{1-10}$ acyloxy;

$R_7$ and $R_8$ are independently selected from the group consisting of hydrogen, hydroxy, alkoxy, thiol, thioalkyl, amino, halogen, cyano, carboxy, alkoxycarbonyl, carbamoyl, $C_{1-6}$ alkyl, $C_{2-6}$ alkenyl, $C_{2-6}$ alkynyl, and $C_{1-10}$ acyloxy; and $R_9$ is selected from the group consisting of hydrogen, hydroxy, alkoxy, amino, halogen, azido, $C_{1-6}$ alkyl, $C_{2-6}$ alkenyl, $C_{2-6}$ alkynyl, and $C_{1-10}$ acyloxy; and Z is S.

13. The process according to claim 12, wherein said halogen is iodine.

14. The process according to claim 12, wherein said Lewis acid is trimethylsilyl iodide.

15. The process according to claim 13 or 14, wherein the purine compound is 6-chloropurine.

16. The process according to claim 5, further comprising reacting the compound of formula (XVI) with a silylated $R_2$-compound in the presence of a Lewis acid, whereby said leaving group is displaced, to produce a compound of formula (XVII):

(XVII)

wherein

Z is S;

R₂ is selected from the group consisting of:

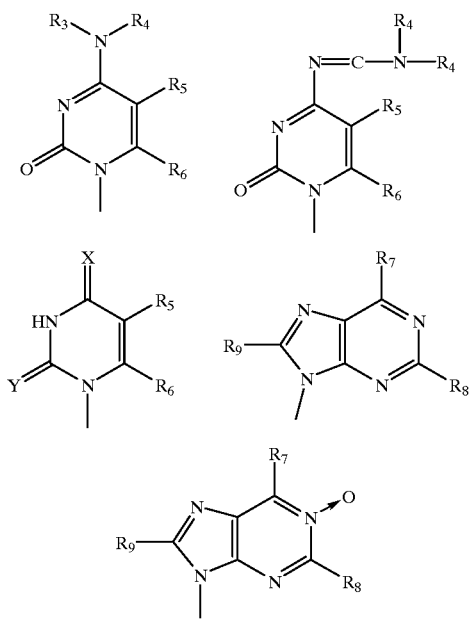

X is oxygen or sulfur;
Y is oxygen or sulfur;
R₃ and R₄ are independently selected from the group consisting of hydrogen, hydroxyl, amino, $C_{1-6}$ alkyl, $C_{2-6}$ alkenyl, $C_{2-6}$ alkynyl, and $C_{1-10}$ acyl or aracyl;
R₅ and R₆ are independently selected from the group consisting of hydrogen, halogen, hydroxyl, amino, cyano, carboxy, carbamoyl, alkoxycarbonyl, hydroxymethyl, trifluoromethyl, thioaryl, $C_{1-6}$ alkyl, $C_{2-6}$ alkenyl, $C_{2-6}$ alkynyl, and $C_{1-10}$ acyloxy;
R₇ and R₈ are independently selected from the group consisting of hydrogen, hydroxy, alkoxy, thiol, thioalkyl, amino, halogen, cyano, carboxy, alkoxycarbonyl, carbamoyl, $C_{1-6}$ alkyl, $C_{2-6}$ alkenyl, $C_{2-6}$ alkynyl, and $C_{1-10}$ acyloxy; and
R₉ is selected from the group consisting of hydrogen, hydroxy, alkoxy, amino, halogen, azido, $C_{1-6}$ alkyl, $C_{2-6}$ alkenyl, $C_{2-6}$ alkynyl, and $C_{1-10}$ acyloxy.

17. The process according to claim 16, further comprising oxidizing Z of the compound of formula (XVII) to give a compound of formula (XVII) wherein Z is S=O or SO₂.

18. The process according to claim 16, wherein the Lewis acid is selected from the group consisting of: TMSOTf, TMSI, TiCl₄ and SnCl₄.

19. The process according to claim 16, further comprising optionally oxidizing Z of the compound of formula (XVII) to give a compound of formula XVII wherein Z is S=O or SO₂ and
reducing the R_yO₂C group of the compound of formula (XVII) to obtain a compound of formula (I):

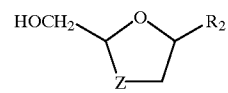

wherein:
Z is selected from the group consisting of S, S=O and SO₂.

20. The process according to claim 19, wherein R₂ is uracil and further comprising the steps of:
(a) protecting the hydroxyl group of the compound of formula (I) with a protecting function R₁ to obtain a compound of formula (XIX):

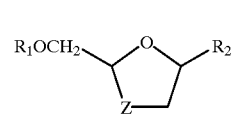

wherein R₁ is selected from the group consisting of $C_{1-16}$ acyl, t-butyldimethylsilyl, and t-butyldiphenylsilyl;
(b) interconverting the uracil group R₂ of formula (XIX) to a cytosine group, designated as $R_{2a}$, to obtain a compound of formula (XX):

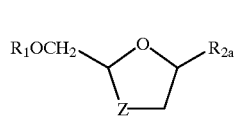

and (c) removing the protecting function R₁ of the compound of formula (XX) to obtain a compound of formula (I'):

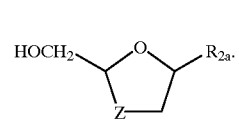

21. A process comprising:
combining 1,4-dithiane-2,5-diol, in a solvent, with a compound of formula R_yOOCCHO, wherein R_y is $C_{1-12}$ alkyl or $C_{6-20}$ aryl to obtain a compound of formula (XV)

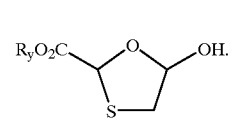

22. A process according to claim 21, wherein said compound of formula R_yOOCCHO is ethyl gloxylate.

* * * * *